US008700130B2

(12) United States Patent
Iddan et al.

(10) Patent No.: US 8,700,130 B2

(45) Date of Patent: Apr. 15, 2014

(54) STEPWISE ADVANCEMENT OF A MEDICAL TOOL

(75) Inventors: Gavriel Iddan, Haifa (IL); David Tolkowsky, Tel Aviv (IL); Ran Cohen, Petah Tikva (IL); Jacob Blank, Ramat HaSharon (IL)

(73) Assignee: Sync-RX, Ltd., Netanya (IL)

( * ) Notice: Subject to any disclaimer, the term of this patent is extended or adjusted under 35 U.S.C. 154(b) by 1190 days.

(21) Appl. No.: 12/487,315

(22) Filed: Jun. 18, 2009

(65) Prior Publication Data

US 2009/0306547 A1 Dec. 10, 2009

Related U.S. Application Data

(63) Continuation-in-part of application No. PCT/IL2008/000316, filed on Mar. 9, 2008, and a continuation-in-part of application No. 12/075,244, filed on Mar. 10, 2008, and a continuation-in-part of application No. 12/075,214, filed on Mar. 10, 2008, (Continued)

(51) Int. Cl.

| | |
|---|---|
| ***A61B 5/06*** | (2006.01) |
| ***A61M 25/09*** | (2006.01) |
| *A61B 8/02* | (2006.01) |

(52) U.S. Cl.

CPC ............ *A61B 5/06* (2013.01); *A61M 25/09041* (2013.01); *A61B 8/02* (2013.01)

USPC ............................ 600/424; 600/434; 600/428

(58) Field of Classification Search

CPC .............................. A61B 5/06; A61B 19/5244

USPC .......................................................... 600/424

See application file for complete search history.

(56) References Cited

U.S. PATENT DOCUMENTS 3,871,360 A 3/1975 Van Horn et al.
3,954,098 A 5/1976 Dick et al.

(Continued)

FOREIGN PATENT DOCUMENTS

EP 2 570 079 A1 3/2013
WO WO 94/10904 5/1994

(Continued)

OTHER PUBLICATIONS

Official Action dated Aug. 27, 2012, which issued during the prosecution U.S. Appl. No. 12/075,214.

(Continued)

*Primary Examiner* — Tse Chen
*Assistant Examiner* — Patricia Park
(74) *Attorney, Agent, or Firm* — Sughrue Mion, PLLC

(57) ABSTRACT

Apparatus is provided, including a sensor for sensing a phase of cyclic activity of a subject's body system. A tool modulator includes a gate configured:

in a first cycle of the cyclic activity, to allow movement of a tool, in response to the cyclic activity being at a first given phase thereof, following the given phase in the first cycle and prior to an occurrence of the given phase in a subsequent cycle of the cyclic activity, to inhibit the movement of the tool, and in a second cycle of the cyclic activity, subsequent to the inhibiting of the movement, to allow movement of the tool, in response to the second cycle of the cyclic activity being at the given phase thereof.

An accumulation facilitator facilitates an accumulation of the tool in the tool modulator, and/or an accumulation of energy in the tool.

36 Claims, 7 Drawing Sheets

Related U.S. Application Data and a continuation-in-part of application No. 12/075,252, filed on Mar. 10, 2008.

(60) Provisional application No. 60/906,091, filed on Mar. 8, 2007, provisional application No. 60/924,609, filed on May 22, 2007, provisional application No. 60/929,165, filed on Jun. 15, 2007, provisional application No. 60/935,914, filed on Sep. 6, 2007, provisional application No. 60/996,746, filed on Dec. 4, 2007, provisional application No. 61/129,331, filed on Jun. 19, 2008.

(56) References Cited

U.S. PATENT DOCUMENTS

| | | | | |
|---|---|---|---|---|
| 4,016,871 | A | 4/1977 | Schiff | |
| 4,031,884 | A | 6/1977 | Henzel | |
| 4,245,647 | A | 1/1981 | Randall | |
| 4,270,143 | A | 5/1981 | Morris | |
| 4,316,218 | A | 2/1982 | Gay | |
| 4,382,184 | A | 5/1983 | Wernikoff | |
| 4,545,390 | A | 10/1985 | Leary | |
| 4,709,385 | A | 11/1987 | Pfeiler | |
| 4,712,560 | A | 12/1987 | Schaefer et al. | |
| 4,723,938 | A | 2/1988 | Goodin et al. | |
| 4,758,223 | A | 7/1988 | Rydell | |
| 4,849,906 | A | 7/1989 | Chodos et al. | |
| 4,865,043 | A | 9/1989 | Shimoni | |
| 4,878,115 | A | 10/1989 | Elion | |
| 4,920,413 | A | 4/1990 | Nakamura | |
| 4,991,589 | A | 2/1991 | Hongo et al. | |
| 4,994,965 | A | 2/1991 | Crawford et al. | |
| 5,020,516 | A | 6/1991 | Biondi | |
| 5,054,045 | A | 10/1991 | Whiting et al. | |
| 5,054,492 | A | 10/1991 | Scribner | |
| 5,062,056 | A | 10/1991 | Lo et al. | |
| 5,176,619 | A | 1/1993 | Segalowitz | |
| 5,177,796 | A | 1/1993 | Feig et al. | |
| 5,293,574 | A | 3/1994 | Roehm et al. | |
| 5,295,486 | A | 3/1994 | Wollschlager et al. | |
| 5,330,496 | A | 7/1994 | Alferness | |
| 5,357,550 | A | 10/1994 | Asahina et al. | |
| 5,429,144 | A | 7/1995 | Wilk | |
| 5,457,728 | A | 10/1995 | Whiting et al. | |
| 5,457,754 | A | 10/1995 | Han et al. | |
| 5,486,192 | A | 1/1996 | Walinsky et al. | |
| 5,537,490 | A | 7/1996 | Yukawa | |
| 5,538,494 | A | 7/1996 | Matsuda | |
| 5,577,502 | A | 11/1996 | Darrow et al. | |
| 5,586,201 | A | 12/1996 | Whiting et al. | |
| 5,596,990 | A | 1/1997 | Yock | |
| 5,613,492 | A | 3/1997 | Feinberg | |
| 5,619,995 | A | 4/1997 | Lobodzinski | |
| 5,630,414 | A | 5/1997 | Horbaschek | |
| 5,674,217 | A | 10/1997 | Walhstrom et al. | |
| 5,724,977 | A | 3/1998 | Yock | |
| 5,764,723 | A | 6/1998 | Weinberger | |
| 5,766,208 | A | 6/1998 | McEwan | |
| 5,792,157 | A * | 8/1998 | Mische et al. | 606/159 |
| 5,809,105 | A | 9/1998 | Roehm et al. | |
| 5,822,391 | A | 10/1998 | Whiting et al. | |
| 5,830,222 | A | 11/1998 | Makower | |
| 5,879,305 | A | 3/1999 | Yock | |
| 5,885,218 | A | 3/1999 | Teo | |
| 5,916,194 | A * | 6/1999 | Jacobsen et al. | 604/96.01 |
| 5,921,934 | A | 7/1999 | Teo | |
| 5,971,976 | A | 10/1999 | Wang et al. | |
| 6,088,488 | A | 7/2000 | Hardy et al. | |
| 6,095,976 | A | 8/2000 | Nachtomy | |
| 6,120,455 | A | 9/2000 | Teo | |
| 6,126,608 | A | 10/2000 | Kemme et al. | |
| 6,148,095 | A | 11/2000 | Prause et al. | |
| 6,152,878 | A | 11/2000 | Nachtomy | |
| 6,195,445 | B1 | 2/2001 | Dubuisson-Jolly et al. | |
| 6,233,478 | B1 | 5/2001 | Liu | |
| 6,246,898 | B1 | 6/2001 | Vesely et al. | |
| 6,254,541 | B1 | 7/2001 | Teo | |
| 6,267,727 | B1 | 7/2001 | Teo | |
| 6,331,181 | B1 | 12/2001 | Tierney et al. | |
| 6,370,417 | B1 | 4/2002 | Horbaschek et al. | |
| 6,377,011 | B1 | 4/2002 | Ben-Ur | |
| 6,442,415 | B1 | 8/2002 | Bis et al. | |
| 6,454,715 | B2 | 9/2002 | Teo | |
| 6,454,776 | B1 | 9/2002 | Tajima et al. | |
| 6,473,635 | B1 | 10/2002 | Rasche | |
| 6,491,636 | B2 | 12/2002 | Chenal | |
| 6,496,716 | B1 | 12/2002 | Langer et al. | |
| 6,532,380 | B1 | 3/2003 | Close et al. | |
| 6,538,634 | B1 * | 3/2003 | Chui et al. | 345/156 |
| 6,589,176 | B2 | 7/2003 | Jago | |
| 6,616,596 | B1 | 9/2003 | Milbocker | |
| 6,643,533 | B2 | 11/2003 | Knoplioch | |
| 6,659,953 | B1 | 12/2003 | Sumanaweera et al. | |
| 6,666,863 | B2 | 12/2003 | Wentzel et al. | |
| 6,704,593 | B2 | 3/2004 | Stainsby | |
| 6,708,052 | B1 | 3/2004 | Mao et al. | |
| 6,711,436 | B1 | 3/2004 | Duhaylongsod | |
| 6,718,055 | B1 | 4/2004 | Suri | |
| 6,726,675 | B1 | 4/2004 | Beyar | |
| 6,728,566 | B1 | 4/2004 | Subramanyan | |
| 6,731,973 | B2 | 5/2004 | Voith | |
| 6,786,896 | B1 | 9/2004 | Madhani et al. | |
| 6,788,827 | B1 | 9/2004 | Makram-Ebeid | |
| 6,796,972 | B1 | 9/2004 | Sinofsky et al. | |
| 6,835,177 | B2 | 12/2004 | Fritz et al. | |
| 6,858,003 | B2 | 2/2005 | Evans et al. | |
| 6,912,471 | B2 | 6/2005 | Heigl | |
| 6,937,696 | B1 | 8/2005 | Mostafavi | |
| 6,959,266 | B1 | 10/2005 | Mostafavi | |
| 6,973,202 | B2 | 12/2005 | Mostafavi | |
| 6,980,675 | B2 | 12/2005 | Evron et al. | |
| 6,996,430 | B1 | 2/2006 | Gilboa et al. | |
| 6,999,852 | B2 | 2/2006 | Green | |
| 7,031,504 | B1 | 4/2006 | Argiro et al. | |
| 7,070,555 | B2 | 7/2006 | Siess | |
| 7,085,342 | B2 | 8/2006 | Younis et al. | |
| 7,134,994 | B2 | 11/2006 | Alpert | |
| 7,155,046 | B2 | 12/2006 | Aben et al. | |
| 7,155,315 | B2 | 12/2006 | Niemeyer et al. | |
| 7,180,976 | B2 | 2/2007 | Wink et al. | |
| 7,191,100 | B2 | 3/2007 | Mostafavi | |
| 7,209,779 | B2 | 4/2007 | Kaufman | |
| 7,215,802 | B2 | 5/2007 | Klingensmith | |
| 7,269,457 | B2 | 9/2007 | Shafer | |
| 7,289,652 | B2 | 10/2007 | Florent et al. | |
| 7,321,677 | B2 | 1/2008 | Evron et al. | |
| 7,339,585 | B2 | 3/2008 | Verstraelen et al. | |
| 7,343,032 | B2 | 3/2008 | Oakley et al. | |
| 7,359,554 | B2 | 4/2008 | Klingensmith | |
| 7,369,691 | B2 | 5/2008 | Kondo et al. | |
| 7,397,935 | B2 | 7/2008 | Kimmel | |
| 7,517,318 | B2 | 4/2009 | Altmann | |
| 7,546,154 | B2 | 6/2009 | Hornegger et al. | |
| 7,587,074 | B2 | 9/2009 | Zarkh et al. | |
| 7,599,730 | B2 | 10/2009 | Hunter | |
| 7,604,601 | B2 | 10/2009 | Altmann | |
| 7,693,349 | B2 | 4/2010 | Gering | |
| 7,697,974 | B2 | 4/2010 | Jenkins | |
| 7,713,210 | B2 | 5/2010 | Byrd | |
| 7,729,743 | B2 | 6/2010 | Sabczynski et al. | |
| 7,729,746 | B2 | 6/2010 | Redel et al. | |
| 7,740,584 | B2 | 6/2010 | Donaldson | |
| 7,773,787 | B2 | 8/2010 | Tek et al. | |
| 7,773,792 | B2 | 8/2010 | Kimmel | |
| 7,778,488 | B2 | 8/2010 | Nord | |
| 7,778,688 | B2 | 8/2010 | Strommer | |
| 7,822,291 | B2 | 10/2010 | Guetter | |
| 7,831,076 | B2 | 11/2010 | Altmann | |
| 7,848,553 | B2 | 12/2010 | Hertel | |
| 7,877,132 | B2 | 1/2011 | Rongen | |
| 7,916,912 | B2 | 3/2011 | Abramov et al. | |
| 7,925,064 | B2 | 4/2011 | Cloutier et al. | |
| 7,927,275 | B2 | 4/2011 | Kuban | |

(56) References Cited

U.S. PATENT DOCUMENTS

| | | | |
|---|---|---|---|
| 7,930,014 | B2 | 4/2011 | Huennekens et al. |
| 7,935,055 | B2 | 5/2011 | Burckhardt |
| 7,961,926 | B2 | 6/2011 | Viswanathan |
| 7,965,905 | B2 | 6/2011 | Allon et al. |
| 7,970,187 | B2 | 6/2011 | Puts |
| 7,978,916 | B2 | 7/2011 | Klingensmith |
| 7,992,100 | B2 | 8/2011 | Lundstrom |
| 8,029,447 | B2 | 10/2011 | Kanz |
| 8,050,474 | B2 | 11/2011 | Baumgart |
| 8,052,605 | B2 | 11/2011 | Muller |
| 8,055,327 | B2 | 11/2011 | Strommer et al. |
| 8,077,939 | B2 | 12/2011 | Le Nezet et al. |
| 8,086,000 | B2 | 12/2011 | Weijers |
| 8,155,411 | B2 | 4/2012 | Hof |
| 8,157,742 | B2 | 4/2012 | Taylor |
| 8,165,361 | B2 | 4/2012 | Li |
| 8,172,763 | B2 | 5/2012 | Nelson |
| 8,189,886 | B2 | 5/2012 | Huo et al. |
| 8,199,981 | B2 | 6/2012 | Koptenko et al. |
| 8,200,040 | B2 | 6/2012 | Pfister |
| 8,233,718 | B2 | 7/2012 | Klingensmith |
| 8,271,068 | B2 | 9/2012 | Khamene |
| 8,275,201 | B2 | 9/2012 | Rangawala et al. |
| 8,289,284 | B2 | 10/2012 | Glynn |
| 8,298,147 | B2 | 10/2012 | Huennekens |
| 8,303,503 | B2 | 11/2012 | Nair |
| 8,364,242 | B2 | 1/2013 | Li |
| 8,396,276 | B2 | 3/2013 | Gatta |
| 8,409,098 | B2 | 4/2013 | Olson |
| 8,428,318 | B2 | 4/2013 | Zhuo |
| 8,428,691 | B2 | 4/2013 | Byrd |
| 8,433,115 | B2 | 4/2013 | Chen |
| 8,457,374 | B2 | 6/2013 | Lendl |
| 8,478,387 | B2 | 7/2013 | Xu |
| 8,483,488 | B2 | 7/2013 | Richter |
| 2001/0031919 | A1 | 10/2001 | Strommer et al. |
| 2002/0049375 | A1 | 4/2002 | Strommer et al. |
| 2002/0058869 | A1 | 5/2002 | Axelsson et al. |
| 2002/0188307 | A1 | 12/2002 | Pintor et al. |
| 2003/0014100 | A1 | 1/2003 | Maria Meens et al. |
| 2003/0018251 | A1 | 1/2003 | Solomon |
| 2003/0023141 | A1 | 1/2003 | Stelzer et al. |
| 2003/0069499 | A1 | 4/2003 | Lienard et al. |
| 2003/0088179 | A1 | 5/2003 | Seeley et al. |
| 2003/0157073 | A1 | 8/2003 | Peritt et al. |
| 2004/0034380 | A1 | 2/2004 | Woolfson et al. |
| 2004/0077941 | A1 | 4/2004 | Reddy et al. |
| 2004/0097805 | A1 | 5/2004 | Verard et al. |
| 2004/0176681 | A1 | 9/2004 | Mao et al. |
| 2004/0249270 | A1 | 12/2004 | Kondo et al. |
| 2004/0254570 | A1 | 12/2004 | Hadjicostis et al. |
| 2004/0267113 | A1 | 12/2004 | Thomson |
| 2005/0004503 | A1 | 1/2005 | Samson et al. |
| 2005/0008210 | A1 | 1/2005 | Evron et al. |
| 2005/0031176 | A1 | 2/2005 | Hertel |
| 2005/0033199 | A1* | 2/2005 | van der Steen et al. ....... 600/587 |
| 2005/0043614 | A1 | 2/2005 | Huizenga et al. |
| 2005/0054916 | A1 | 3/2005 | Mostafavi |
| 2005/0080336 | A1 | 4/2005 | Byrd et al. |
| 2005/0090737 | A1 | 4/2005 | Burrel et al. |
| 2005/0096589 | A1 | 5/2005 | Shacar |
| 2005/0107688 | A1 | 5/2005 | Strommer |
| 2005/0111719 | A1 | 5/2005 | Pescatore et al. |
| 2005/0137661 | A1 | 6/2005 | Sra |
| 2005/0143777 | A1 | 6/2005 | Sra |
| 2005/0197557 | A1 | 9/2005 | Strommer et al. |
| 2005/0197566 | A1* | 9/2005 | Strommer et al. ............ 600/424 |
| 2005/0201510 | A1 | 9/2005 | Mostafavi |
| 2005/0228359 | A1 | 10/2005 | Doyle |
| 2005/0234331 | A1 | 10/2005 | Sendai |
| 2005/0273050 | A1 | 12/2005 | Yokoyama et al. |
| 2005/0288577 | A1 | 12/2005 | Weese |
| 2006/0058647 | A1 | 3/2006 | Strommer et al. |
| 2006/0074285 | A1 | 4/2006 | Zarkh et al. |
| 2006/0120581 | A1 | 6/2006 | Eck et al. |
| 2006/0129142 | A1 | 6/2006 | Reynolds |
| 2006/0147897 | A1 | 7/2006 | Grinvald |
| 2006/0165270 | A1 | 7/2006 | Borgert et al. |
| 2006/0173287 | A1 | 8/2006 | Sabszynski et al. |
| 2006/0184016 | A1 | 8/2006 | Glossop |
| 2006/0224188 | A1 | 10/2006 | Libbus et al. |
| 2006/0241445 | A1 | 10/2006 | Altmann |
| 2006/0241465 | A1 | 10/2006 | Huennekens et al. |
| 2006/0241478 | A1 | 10/2006 | Lewis |
| 2006/0253024 | A1 | 11/2006 | Altmann |
| 2006/0253029 | A1 | 11/2006 | Altmann |
| 2006/0253031 | A1 | 11/2006 | Altmann |
| 2006/0259137 | A1 | 11/2006 | Artof et al. |
| 2006/0269108 | A1 | 11/2006 | Viswanathan |
| 2006/0287595 | A1 | 12/2006 | Maschke |
| 2007/0038061 | A1 | 2/2007 | Huennekens et al. |
| 2007/0043292 | A1 | 2/2007 | Camus |
| 2007/0053558 | A1 | 3/2007 | Puts et al. |
| 2007/0055128 | A1 | 3/2007 | Glossop |
| 2007/0088431 | A1 | 4/2007 | Bourang et al. |
| 2007/0106146 | A1 | 5/2007 | Altmann et al. |
| 2007/0116342 | A1 | 5/2007 | Zarkh et al. |
| 2007/0123771 | A1 | 5/2007 | Redel et al. |
| 2007/0142907 | A1 | 6/2007 | Moaddeb et al. |
| 2007/0173861 | A1 | 7/2007 | Strommer |
| 2007/0208388 | A1 | 9/2007 | Jahns |
| 2007/0219630 | A1 | 9/2007 | Chu |
| 2007/0232896 | A1 | 10/2007 | Gilboa et al. |
| 2007/0248253 | A1 | 10/2007 | Manzke et al. |
| 2007/0255139 | A1 | 11/2007 | Deschinger |
| 2007/0276216 | A1 | 11/2007 | Beyar et al. |
| 2008/0008366 | A1 | 1/2008 | Desh |
| 2008/0015677 | A1 | 1/2008 | Glossop et al. |
| 2008/0021331 | A1 | 1/2008 | Grinvald |
| 2008/0082049 | A1* | 4/2008 | Evans et al. .............. 604/164.13 |
| 2008/0089566 | A1 | 4/2008 | Node-Langlois |
| 2008/0119922 | A1 | 5/2008 | Alkhatib |
| 2008/0137935 | A1 | 6/2008 | Spahn |
| 2008/0146923 | A1 | 6/2008 | Mejia |
| 2008/0146942 | A1 | 6/2008 | Dala-Krishna |
| 2008/0177183 | A1 | 7/2008 | Courtney |
| 2008/0188739 | A1 | 8/2008 | Rongen et al. |
| 2008/0221439 | A1 | 9/2008 | Iddan et al. |
| 2008/0221440 | A1 | 9/2008 | Iddan et al. |
| 2008/0221442 | A1 | 9/2008 | Tolkowsky et al. |
| 2008/0267475 | A1 | 10/2008 | Lendl |
| 2008/0300487 | A1 | 12/2008 | Govari |
| 2009/0103682 | A1 | 4/2009 | Chen et al. |
| 2009/0105579 | A1 | 4/2009 | Garibaldi |
| 2009/0171201 | A1 | 7/2009 | Olson |
| 2009/0177444 | A1 | 7/2009 | Wiemker et al. |
| 2009/0257631 | A1 | 10/2009 | Baumgart |
| 2009/0264753 | A1 | 10/2009 | Von Schulthes |
| 2009/0275831 | A1 | 11/2009 | Hall |
| 2009/0281418 | A1 | 11/2009 | Ruijters et al. |
| 2009/0299195 | A1 | 12/2009 | Muller et al. |
| 2010/0041949 | A1 | 2/2010 | Tolkowsky |
| 2010/0049034 | A1 | 2/2010 | Eck et al. |
| 2010/0054573 | A1 | 3/2010 | Shekhara |
| 2010/0067768 | A1 | 3/2010 | Ionasec et al. |
| 2010/0094124 | A1 | 4/2010 | Schoonenberg et al. |
| 2010/0094127 | A1 | 4/2010 | Xu |
| 2010/0099979 | A1 | 4/2010 | Schoonenberg et al. |
| 2010/0114289 | A1 | 5/2010 | Camus |
| 2010/0123715 | A1 | 5/2010 | Hansegard |
| 2010/0134517 | A1 | 6/2010 | Saikaly et al. |
| 2010/0135546 | A1 | 6/2010 | Cziria |
| 2010/0157041 | A1 | 6/2010 | Klaiman et al. |
| 2010/0160764 | A1 | 6/2010 | Steinberg et al. |
| 2010/0160773 | A1 | 6/2010 | Cohen et al. |
| 2010/0161022 | A1 | 6/2010 | Tolkowsky |
| 2010/0161023 | A1 | 6/2010 | Cohen et al. |
| 2010/0171819 | A1 | 7/2010 | Tolkowsky et al. |
| 2010/0172556 | A1 | 7/2010 | Cohen et al. |
| 2010/0174192 | A1 | 7/2010 | Azuma |
| 2010/0191102 | A1 | 7/2010 | Steinberg et al. |
| 2010/0198063 | A1 | 8/2010 | Huber |
| 2010/0220917 | A1 | 9/2010 | Steinberg et al. |
| 2010/0222671 | A1 | 9/2010 | Cohen et al. |

(56) References Cited

U.S. PATENT DOCUMENTS

| | | | |
|---|---|---|---|
| 2010/0228076 | A1 | 9/2010 | Blank et al. |
| 2010/0246910 | A1 | 9/2010 | Wiemker |
| 2010/0290693 | A1 | 11/2010 | Cohen et al. |
| 2010/0310140 | A1 | 12/2010 | Schneider |
| 2010/0331670 | A1 | 12/2010 | Strommer et al. |
| 2011/0026786 | A1 | 2/2011 | Mohamed |
| 2011/0033094 | A1 | 2/2011 | Zarkh |
| 2011/0034801 | A1 | 2/2011 | Baumgart |
| 2011/0052030 | A1 | 3/2011 | Bruder et al. |
| 2011/0075912 | A1 | 3/2011 | Rieber et al. |
| 2011/0087104 | A1 | 4/2011 | Moore |
| 2011/0157154 | A1 | 6/2011 | Bernard et al. |
| 2011/0228992 | A1 | 9/2011 | Wels et al. |
| 2011/0293163 | A1 | 12/2011 | Kargar et al. |
| 2011/0319752 | A1 | 12/2011 | Steinberg et al. |
| 2012/0004529 | A1 | 1/2012 | Tolkowsky et al. |
| 2012/0004533 | A1 | 1/2012 | Peng |
| 2012/0004537 | A1 | 1/2012 | Tolkowsky et al. |
| 2012/0014574 | A1 | 1/2012 | Ferschel et al. |
| 2012/0029339 | A1 | 2/2012 | Cohen et al. |
| 2012/0051606 | A1 | 3/2012 | Saikia |
| 2012/0059220 | A1 | 3/2012 | Holsing |
| 2012/0059253 | A1 | 3/2012 | Wang et al. |
| 2012/0065507 | A1 | 3/2012 | Brunke |
| 2012/0072190 | A1 | 3/2012 | Sharma et al. |
| 2012/0123238 | A1 | 5/2012 | Vaillant et al. |
| 2012/0130242 | A1 | 5/2012 | Burgess |
| 2012/0140998 | A1 | 6/2012 | Zhu |
| 2012/0207367 | A1 | 8/2012 | Kneepkens |
| 2012/0215093 | A1 | 8/2012 | Ji |
| 2012/0224751 | A1 | 9/2012 | Kemp |
| 2012/0245460 | A1 | 9/2012 | Slomka |
| 2013/0004044 | A1 | 1/2013 | Ross |
| 2013/0030295 | A1 | 1/2013 | Huennekens |
| 2013/0046167 | A1 | 2/2013 | Shah |
| 2013/0109958 | A1 | 5/2013 | Baumgart |
| 2013/0109959 | A1 | 5/2013 | Baumgart |
| 2013/0120296 | A1 | 5/2013 | Merrit |
| 2013/0120297 | A1 | 5/2013 | Merrit |
| 2013/0123616 | A1 | 5/2013 | Merrit |

FOREIGN PATENT DOCUMENTS

| | | | |
|---|---|---|---|
| WO | 99/07354 | A2 | 2/1999 |
| WO | 00/33755 | A1 | 6/2000 |
| WO | 01/10313 | A1 | 2/2001 |
| WO | WO 01/43642 | | 6/2001 |
| WO | 03/043516 | A2 | 5/2003 |
| WO | WO 03/096894 | | 11/2003 |
| WO | WO 2005/026891 | | 3/2005 |
| WO | 2005051452 | A2 | 6/2005 |
| WO | WO 2005/124689 | | 12/2005 |
| WO | 2006/027781 | A2 | 3/2006 |
| WO | WO 2006/066122 | | 6/2006 |
| WO | WO 2006/066124 | | 6/2006 |
| WO | 2006/076409 | A2 | 7/2006 |
| WO | WO 2006/121984 | | 11/2006 |
| WO | 2007/002685 | A2 | 1/2007 |
| WO | 2007/014028 | A1 | 2/2007 |
| WO | 2008/007350 | A1 | 1/2008 |
| WO | WO 2008/007350 | | 1/2008 |
| WO | WO 2008/107905 | | 9/2008 |
| WO | WO 2009/153794 | | 12/2009 |
| WO | WO 2010/058398 | | 5/2010 |
| WO | 2011/046903 | A2 | 4/2011 |
| WO | 2011/046904 | A1 | 4/2011 |
| WO | 2012/028190 | A1 | 3/2012 |
| WO | 2012/138872 | A2 | 10/2012 |
| WO | 2012/138874 | A2 | 10/2012 |
| WO | 2013/025602 | A1 | 2/2013 |

OTHER PUBLICATIONS

Official Action dated Oct. 31, 2012, which issued during the prosecution U.S. Appl. No. 12/075,244.

Official Action dated Sep. 20, 2012, which issued during the prosecution of U.S. Appl. No. 12/649,955.

International Search Report dated Oct. 10, 2012, which issued during the prosecution of PCT/IL2012/000246.

Communication dated Sep. 5, 2012 , which issued during the prosecution of EP Application 09 766 329.8-1526.

Communication dated Oct. 29, 2012 , which issued during the prosecution of EP Application 08 719941.0-1265/2129284.

Official Action dated Oct. 23, 2012, which issued during the prosecution of JP Application No. 2009-552328.

Computer translation of JP 2010-253017 to Takeshi.

W. Goodman et al., "Coronary-Artery Calcification in Young Adults With End-Stage Renal Disease Who Are Undergoing Dialysis," The New England Journal of Medicine, vol. 342 No. 20.

W. Santamore et al., "A microcomputer based automated quantative coronary angiographic analysis system," Annals of Biomedical Engineering, vol. 16, pp. 367-377, 1988.

I. Kompatsiaris et al., "Deformable Boundary Detection of Stents in Angiographic Images," IEEE Transactions on Medical Imaging, vol. 19, No. 6, Jun. 2000.

V. Duddalwar, "Multislice CT angiography: a practical guide to CT angiography in vascular imaging and intervention," The British Journal of Radiology, 77 (2004), S27-S38.

W. Leung et al., "Coronary Artery Quantitation and Data Management System for Paired Cineangiograms," Catheterization and Cardiovascular Diagnosis 24:121-134 (1991).

G. Mancini et al., "Automated quantitative coronary arteriography: morphologic and physiologic validation in vivo of a rapid digital angiographic method," Circulation 1987;75:452-460.

L. Yaneza et al., "Atherosclerotic Plaque Can Be Quantified Using Multifractal and Wavelet Decomposition Techniques," ABSTRACTS—Angiography & Interventional Cardiology, JACC Mar. 3, 2004.

Official Action dated Nov. 23, 2012, which issued during the prosecution of U.S. Appl. No. 12/649,944.

U.S. Appl. No. 61/359,431.

Boyle et al., entitled "Assessment of a Novel Angiographic Image Stabilization System for Percutaneous Coronary Intervention" (Journal of Interventional Cardiology, vol. 20 No. 2, 2007.

Timinger et al., entitled "Motion compensated coronary interventional navigation by means of diaphragm tracking and elastic motion models" (Phys Med Biol. Feb. 7, 2005;50(3):491-503.

Timinger et al., entitled "Motion compensation for interventional navigation on 3D static roadmaps based on an affine model and gating" (Phys Med Biol. Mar. 7, 2004;49(5):719-32.

Turski et al., entitled "Digital Subtraction Angiography 'Road Map'" (American Journal of Roentgenology, 1982.

Iddan et al., entitled "3D imaging in the studio and elsewhere" (SPIE Proceedings vol. 4298, 2001.

"Catheter Insertion Simulation with Combined Visual and Haptic Feedback," by Zorcolo et al. (Center for Advanced Studies, Research and Development in Sardinia).

"4D-CT imaging of a volume influenced by respiratory motion on multi-slice CT Tinsu Pan," by Lee et al., (Medical Physics, Feb. 2004, vol. 31, Issue 2, pp. 333-340)—an abstract.

"New 4-D imaging for real-time intraoperative MRI: adaptive 4-D scan," by Tokuda et al. (Med Image Comput Assist Intery Int Conf. 2006;9(Pt 1):454-61) an abstract.

"Real-time interactive viewing of 4D kinematic MR joint studies," by Schulz et al. (Med Image Comput Assist Intery Int Conf. 2005;8(Pt 1):467-73.)—an abstract.

"4D smoothing of gated SPECT images using a left-ventricle shape model and a deformable mesh," by Brankov et al., (Nuclear Science Symposium Conference Record, 2004 IEEE, Oct. 2004, vol. 5, 2845-2848).

"Prospective motion correction of X-ray images for coronary interventions," by Shechter et al. (IEEE Trans Med Imaging. Apr. 2005;24(4):441-50).

"Cardiac Imaging: We Got the Beat!" by Elizabeth Morgan (Medical Imaging, Mar. 2005).

"Noninvasive Coronary Angiography by Retrospectively ECG-Gated Multislice Spiral CT," by Achenbach et al., (Circulation. Dec. 5, 2000;102(23):2823-8).

(56) References Cited

OTHER PUBLICATIONS

"Spatially-adaptive temporal smoothing for reconstruction of dynamic and gated image sequences," by Brankov et al., (Nuclear Science Symposium Conference Record, 2000 IEEE, 2000, vol. 2, 15/146-15/150)—an abstract.
"Full-scale clinical implementation of a video based respiratory gating system," by Ramsey et al., (Engineering in Medicine and Biology Society, 2000. Proceedings of the 22nd Annual International Conference of the IEEE, 2000, vol. 3, 2141-2144)—an abstract.
"Three-Dimensional Respiratory-Gated MR Angiography of the Coronary Arteries: Comparison with Conventional Coronary Angiography," by Post et al., (AJR, 1996; 166: 1399-1404).
Soffie Mansson, et al., "Dosimetric verification of breathing adapted radiotherapy using polymer gel", Journal of Physics: Conference series 56 (200) 300-303.
"From 2D to 4D" Axiom Innovations—Mar. 2008, www.siemens.com/healthcare-magazine.
A Brochure: Impella® 2.5, Percutaneous Circulatory Support System, ABIOMED™, 2007.
Frangi et al., entitled "Multiscale vessel enhancement filtering" (Medical Image Computing and Computer Assisted Intervention—MICCAI 1998—Lecture Notes in Computer Science, vol. 1496, Springer Verlag, Berlin, Germany, pp. 130-137).
Dijkstra, entitled "A Note on Two Problems in Connexion with Graphs" (Numerische Mathematik 1, 269-271, 1959).
Zarkh et al., entitled "Guide wire navigation and therapeutic device localization for catheterization procedure" (International Congress Series 1281 (2005) 311-316.
Brochure: At the Transvascular Cardiovascular Therapeutics (TCT) conference held in Washington DC, USA in Oct. 2008, Paieon Inc. demonstrated the CardiOp-THV system for real-time navigation and positioning of a trans-catheter heart valve.
Brochure: At the TCT conference held in San Francisco, USA in Sep. 2009, Paieon Inc. demonstrated the IC-PRO Comprehensive Imaging Workstation for providing assistance in cardiac catheterization procedures.
An International Search Report dated Sep. 8, 2009, which issued during the prosecution of Applicant's PCT/IL09/00610.
An International Search Report dated Jan. 15, 2009, issued during the prosecution of Applicant's PCT Patent Application No. PCT/IL08/000316.
"Geometrically Correct 3-D Reconstruction of Intravascular Ultrasound Images by Fusion with Biplane Angiography—Methods and Validation," Andreas Wahle, et al., IEEE Transactions on Medical Imaging, Final Manuscript #187/98, Jun. 30, 1999.
International Search Report dated Jan. 6, 2012 issued during the prosecution of PCT Application No. PCT/IL11/00391.
Office Action dated Dec. 8, 2011 issued in U.S. Appl. No. 12/075,244.
Office Action dated Nov. 28, 2011 issued in U.S. Appl. No. 12/075,252.
International Search Report dated Mar. 2, 2012, issued in PCT/IL11/00612.
Office Action dated Mar. 14, 2012, issued in U.S. Appl. No. 12/075,214.
Office Action dated Mar. 15, 2012, issued in U.S. Appl. No. 12/649,944.
Office Action dated Mar. 15, 2012, issued in U.S. Appl. No. 12/650,152.
Office Action dated May 22, 2012, issued in U.S. Appl. No. 12/075,244.
Umeda, H. et al., "Promising efficacy of primary gradual and prolonged balloon angioplasty in small coronary arteries: a randomized comparison with cutting balloon angioplasty and conventional balloon angioplasty", American Heart Journal, vol. 147, No. 1, pp. 1-8, Jan. 2004.
U.S. Appl. No. 60/845,347 to Strommer et al., filed Sep. 2006?.
A Notice of Allowance in Applicant's U.S. Appl. No. 12/781,414.
An Official Action dated Aug. 3, 2012, which issued during the prosecution of Applicant's U.S. Appl. No. 12/781,294.
An Official Action dated Jun. 19, 2012, which issued during the prosecution of Applicant's U.S. Appl. No. 12/075,252.
An Official Action dated Jun. 18, 2012, which issued during the prosecution of Applicant's U.S. Appl. No. 12/781,366.
An Official Action dated Jun. 7, 2012, which issued during the prosecution of Applicant's U.S. Appl. No. 12/650,156.
An Official Action dated May 29, 2012, which issued during the prosecution of Applicant's U.S. Appl. No. 12/650,121.
Buddy D. Ratner, "Biomaterials Science: An Introduction to Materials in Medicine", Elsevier, chapter 7, 1996.
Gerald E. Miller, "Fundamentals of Biomedical Transport Processes, Morgan & Claypool Publishers", chapter 2, 2010.
Gerhard Albert ten Brinke, "Automated coronary flow reserve assessment using planar x-ray angiography", PhD dissertation, Universiteit Twente, 2011.
Jerry T. Wong et al., "Quantification of fractional flow reserve based on angiographic image data", Int J Cardiovasc Imaging 28:13-22, Jan. 7, 2011.
Kassab, G. S. et al., "Cross-sectional area and volume compliance of porcine left coronary arteries," Am. J. Physiol. Heart Circ. Physiol. 281, H623-H628, Aug. 2011.
Molloi S. et al., "Absolute volumetric coronary blood flow measurement with digital subtraction angiography". Int J Card Imaging 14:137-145, 1998.
Molloi, S. et al., "Estimation of coronary artery hyperemic blood flow based on arterial lumen volume using angiographic images," The International Journal of Cardiovascular Imaging, vol. 28, No. 1, 1-11, Jan. 7, 2011.
Molloi, S. et al., "Quantification of coronary artery lumen volume by digital angiography: in vivo validation," Circulation 104, 2351-2357, Nov. 6, 2001.
Molloi, S. et al., "Quantification of volumetric coronary blood flow with dual-energy digital subtraction angiography," Circulation 93, 1919-1927, May 15, 1996.
Molloi, S. et al., "Regional volumetric coronary blood flow measurement by digital angiography: in vivo validation," Acad. Radiol. 11, 7, 757-766, Jul. 2004.
Sian Sen et al., "Development and Validation of a New, Adenosine-Independent Index of Stenosis Severity From Coronary Wave—Intensity Analysis". Journal of the American College of Cardiology, vol. 59, Apr. 10, 2012.
Yunlong Huo et al., "A validated predictive model of coronary fractional flow reserve," J. R. Soc. Interface, Nov. 23, 2011.
A search report dated Nov. 23, 2012 , which issued during the prosecution of Applicant's EP Application 09 827264.4-1265/2358269.
An examination report dated Dec. 5, 2012, which issued during the prosecution of Applicant's EP Application 09766329.8.
An Official Action dated Dec. 10, 2012, which issued during the prosecution of Applicant's U.S. Appl. No. 12/650,156.
An Official Action dated Dec. 11, 2012, which issued during the prosecution of Applicant's U.S. Appl. No. 12/650,152.
An Official Action dated Jan. 22, 2013, which issued during the prosecution of Applicant's U.S. Appl. No. 12/650,121.
An Official Action dated Jan. 28, 2013, which issued during the prosecution of Applicant's U.S. Appl. No. 12/781,366.
An Official Action dated Feb. 4, 2013, which issued during the prosecution of Applicant's U.S. Appl. No. 13/228,185.
An Official Action dated Sep. 6, 2013 , which issued during the prosecution of Applicant's U.S. Appl. No. 12/650,605.
An Official Action dated Aug. 30, 2013, which issued during the prosecution of Applicant's U.S. Appl. No. 12/650,121.
An Official Action dated Sep. 12, 2013, which issued during the prosecution of Applicant's U.S. Appl. No. 12/781,260.
"A new point matching algorithm for non-rigid registration," by Chui (Computer Vision and Image Understanding 89 (2003) 114-141).
"Advanced and Challenges in Super-Resolution," by Farsiu (International Journal of Imaging Systems and Technology, vol. 14, No. 2, pp. 47-57, Special issue on high-resolution image reconstruction, Aug. 2004).
"Image Registration by Minimization of Residual Complexity," by Myronenko (CVPR 2009).
"Image inpainting," by Bertalmio (ACM Siggraph 2000, New Orleans, Louisiana, USA, Jul. 2000).

(56) References Cited

OTHER PUBLICATIONS

"Nonrigid registration using free-form deformations: application to breast MR images," by Rueckert, (IEEE Trans. Med. Img, vol. 18, No. 8, 1999).
"Unwarping of unidirectionally distorted EPI images," by Kybic (IEEE Trans. Med. Img., vol. 19, No. 2, 2000).
An International Search Report dated May 19, 2010 issued during the prosecution of Applicant's PCT Patent Application No. PCT/IL2009/001089.
An Official Action dated Jul. 2, 2013, which issued during the prosecution of Applicant's U.S. Appl. No. 12/075,244.
An Official Action dated Jun. 19, 2013, which issued during the prosecution of Applicant's U.S. Appl. No. 12/075,214.
An Official Action dated May 31, 2013, which issued during the prosecution of Applicant's U.S. Appl. No. 12/075,252.
A Notice of Allowance dated Jun. 4, 2013, which issued in Applicant's U.S. Appl. No. 12/649,960.
Office Action dated Dec. 31, 2013, issued by the USPTO in corresponding U.S. Appl. No. 12/075,252.

* cited by examiner

STEPWISE ADVANCEMENT OF A MEDICAL TOOL

CROSS-REFERENCES TO RELATED APPLICATIONS

The present patent application claims priority of U.S. Provisional Patent Application No. 61/129,331 to Iddan, filed on Jun. 19, 2008, entitled "Stepwise advancement of a medical tool," and is a continuation-in-part of:

(a) PCT Application PCT/IL2008/000316 to Iddan (published as WO 08/107905), filed on Mar. 9, 2008, entitled "Imaging and tools for use with moving organs,"

(b) U.S. patent application Ser. No. 12/075,244 to Tolkowsky (published as US 2008/0221442), filed Mar. 10, 2008, entitled "Imaging for use with moving organs,"

(c) U.S. patent application Ser. No. 12/075,214 to Iddan (published as US 2008/0221439), filed Mar. 10, 2008, entitled "Tools for use with moving organs," and (d) U.S. patent application Ser. No. 12/075,252 to Iddan (published as US 2008/0221440), filed Mar. 10, 2008, entitled "Imaging and tools for use with moving organs,"

all of which claim the benefit of U.S. Provisional Patent Application Nos.:

60/906,091 filed on Mar. 8, 2007,

60/924,609 filed on May 22, 2007,

60/929,165 filed on Jun. 15, 2007,

60/935,914 filed on Sep. 6, 2007, and

60/996,746 filed on Dec. 4, 2007, all entitled "Apparatuses and methods for performing medical procedures on cyclically-moving body organs," and all of which applications are incorporated herein by reference.

FIELD OF THE INVENTION

The present invention generally relates to medical apparatus. Specifically, the present invention relates to stepwise advancement of a medical tool, within a body organ, in accordance with a motion cycle of that organ.

BACKGROUND OF THE INVENTION

Guide wires are commonly used in the course of transcatheter endovascular interventions. Among the usages of such guide wires is the penetration of total or near-total occlusions in a blood vessel, such as an artery. In some cases, the artery moves in accordance with a cyclical physiological cycle, such as the cardiac cycle in the case of a coronary artery, or the respiratory cycle in the case of a renal artery. In some cases, such motion of the artery also comprises a change in its geometrical shape, such as an angle at which it is bent.

PCT Application WO 08/107905 to Iddan, which is incorporated herein by reference, describes apparatus for use with a portion of a subject's body that moves as a result of cyclic activity of a body system. An imaging device acquires a plurality of image frames of the portion. A sensor senses a phase of the cyclic activity. A medical tool performs a function with respect to the portion. A control unit generates a stabilized set of image frames of the medical tool disposed within the portion, actuates the tool to perform the function, or move, in response to the sensor sensing that the cyclic activity is at a given phase thereof, and inhibits the tool from performing the action or moving in response to the sensor sensing that the cyclic activity is not at the given phase. A display facilitates use of the tool by displaying the stabilized set of image frames.

U.S. Pat. No. 4,545,390 to Leary describes a guide wire for guiding a very small diameter catheter, such as a coronary dilatation catheter used in coronary angioplasty techniques.

U.S. Pat. No. 4,758,223 to Rydell describes a hand-operated device for inflating the expander on a balloon-type catheter and for perfusing fluids through the catheter and out its distal end.

U.S. Pat. No. 4,723,938 to Goodin et al. describes an inflation/deflation device for an angioplasty balloon catheter which permits quick inflation to an approximate working pressure followed by a fine but slower adjustment to a final desired pressure.

The following references may be of interest:

U.S. Pat. No. 4,865,043 to Shimoni, U.S. Pat. No. 3,954,098 to Dick et al., U.S. Pat. No. 4,382,184 to Wernikoff, U.S. Pat. No. 4,016,871 to Schiff, U.S. Pat. No. 3,871,360 to Van Horn et al., U.S. Pat. No. 4,031,884 to Henzel, U.S. Pat. No. 4,994,965 to Crawford et al., U.S. Pat. No. 4,878,115 to Elion, U.S. Pat. No. 4,709,385 to Pfeiler, U.S. Pat. No. 4,270,143 to Morris, U.S. Pat. No. 4,758,223 to Rydell, U.S. Pat. No. 4,723,938 to Goodin et al., U.S. Pat. No. 6,937,696 to Mostafavi, U.S. Pat. No. 6,246,898 to Vesely et al., U.S. Pat. No. 6,666,863 to Wentzel et al., U.S. Pat. No. 5,176,619 to Segalowitz, U.S. Pat. No. 5,830,222 to Makower, U.S. Pat. No. 4,245,647 to Randall, U.S. Pat. No. 4,316,218 to Gay, U.S. Pat. No. 4,849,906 to Chodos et al., U.S. Pat. No. 5,062,056 to Lo et al., U.S. Pat. No. 5,630,414 to Horbaschek, U.S. Pat. No. 6,442,415 to Bis et al., U.S. Pat. No. 6,473,635 to Rasche, U.S. Pat. No. 4,920,413 to Nakamura, U.S. Pat. No. 6,233,478 to Liu, U.S. Pat. No. 5,764,723 to Weinberger, U.S. Pat. No. 5,619,995 to Lobodzinski, U.S. Pat. No. 4,991,589 to Hongo et al., U.S. Pat. No. 5,538,494 to Matsuda, U.S. Pat. No. 5,020,516 to Biondi, U.S. Pat. No. 7,209,779 to Kaufman, U.S. Pat. No. 6,858,003 to Evans et al., U.S. Pat. No. 6,786,896 to Madhani et al., U.S. Pat. No. 6,999,852 to Green, U.S. Pat. No. 7,155,315 to Niemeyer et al., U.S. Pat. No. 5,971,976 to Wang et al., U.S. Pat. No. 6,377,011 to Ben-Ur, U.S. Pat. No. 6,711,436 to Duhaylongsod, U.S. Pat. No. 7,269,457 to Shafer, U.S. Pat. No. 6,959,266 to Mostafavi, U.S. Pat. No. 7,191,100 to Mostafavi, U.S. Pat. No. 6,708,052 to Mao et al., U.S. Pat. No. 7,180,976 to Wink et al., U.S. Pat. No. 7,085,342 to Younis et al., U.S. Pat. No. 6,731,973 to Voith, U.S. Pat. No. 6,728,566 to Subramanyan, U.S. Pat. No. 5,766,208 to McEwan, U.S. Pat. No. 6,704,593 to Stainsby, U.S. Pat. No. 6,973,202 to Mostafavi;

US Patent Application Publication 2006/0058647 to Strommer et al., US Patent Application Publication 2007/0173861 to Strommer, US Patent Application Publication 2007/0208388 to Jahns, US Patent Application Publication 2007/0219630 to Chu, US Patent Application Publication 2004/0176681 to Mao et al., US Patent Application Publication 2005/0090737 to Burrel et al., US Patent Application Publication 2006/0287595 to Maschke, US Patent Application Publication 2007/0142907 to Moaddeb et al., US Patent Application Publication 2007/0106146 to Altmann et al., US Patent Application Publication 2005/0054916 to Mostafavi, US Patent Application Publication 2003/0018251 to Solomon, US Patent Application Publication 2002/0049375 to Strommer et al., US Patent Application Publication 2005/0137661 to Sra, US Patent Application Publication 2005/0143777 to Sra, US Patent Application Publication 2004/0077941 to Reddy et al.;

PCT Publication WO 94/010904 to Nardella, PCT Publication WO 06/066122 to Sra, PCT Publication WO 06/066124 to Sra, PCT Publication WO 05/026891 to Mostafavi, PCT Publication WO 01/43642 to Heuscher, PCT Publication WO 03/096894 to Ho et al., PCT Publication WO 05/124689 to Manzke; and "Catheter Insertion Simulation with Combined Visual and Haptic Feedback," by Zorcolo et al. (Center for Advanced Studies, Research and Development in Sardinia)

SUMMARY OF THE INVENTION

When a guide wire is used for penetrating an occlusion within an artery that changes its shape as a result of organ motion, it may result in (a) the guide wire being pushed along the artery, at some phases of the motion cycle, but (b) in an undesirable direction, for example, toward the wall of the artery, at other phases of the motion cycle. In some cases, the ability to penetrate the occlusion with the guide wire is therefore hindered. In other cases, advancement of the guide wire towards the wall of the artery results in a perforation or dissection of the artery's wall. Such perforation or dissection typically creates some amount of clinical risk.

Separately, when a guide wire is steered towards a side branch whose angle relative to the main artery varies in the course of the motion cycle, entering that side branch may require multiple, repeated attempts.

In some embodiments of the present invention, apparatus and methods are provided for the advancement of an endovascular medical tool, such as a guide wire, within a body organ, in accordance with a motion cycle of that organ. In some embodiments, a guide wire is advanced within a coronary artery in synchronization with the cardiac cycle. In some embodiments, a guide wire is advanced within a renal artery in synchronization with the respiratory cycle. In some embodiments, a guide wire is advanced within a carotid artery in synchronization with the cardiac cycle. In some embodiments, a medical tool is advanced through a bronchial lumen in synchronization with the respiratory cycle.

It is hypothesized by the inventors that embodiments of the current invention offer measures for reducing the aforementioned risk of a guide wire being advanced in an undesirable direction. For example, embodiments of the current invention may reduce the aforementioned risk of a guide wire being advanced into the wall of a blood vessel and creating a perforation or a dissection of that wall. It is also hypothesized by the inventors that advancing a guide wire in the synchronized manner described herein will, in some cases, improve the efficacy of the guide wire in penetrating an occlusion. Separately, it is also hypothesized by the inventors that advancing a guide wire in the synchronized manner described herein will, in some cases, facilitate inserting the guide wire into a side branch, the angle of which, relative to the main lumen, varies in the course of the vessel's motion cycle.

In an embodiment, the guide wire is advanced within a coronary vessel in a stepwise manner, only at a selected phase of the cardiac cycle. In an embodiment, the selected phase of the cardiac cycle is a diastolic or end-diastolic phase, when the blood vessels are relatively further spread apart and less twisted. Compared to unsynchronized advancement of the guide wire (for example, continuous advancement of the guide wire throughout the cardiac cycle), synchronized stepwise advancement in a diastolic or end-diastolic phase typically results in the guide wire being advanced, during a greater portion of its forward motion, along the vessel and, during a lesser portion of its forward motion, towards the wall of the vessel. That, in turn, typically reduces the likelihood of the guide wire perforating or dissecting the vessel wall, and typically increases the efficacy of the guide wire penetrating a possible occlusion in the vessel.

In another embodiment, the guide wire is advanced within a carotid vessel in a stepwise manner, only at a selected phase of the cardiac cycle. In yet another embodiment, the guide wire is advanced within a renal vessel in a stepwise manner, only at a selected phase of the respiratory cycle.

The aforementioned selected phase of the cardiac cycle may be sensed by means of the patient's ECG signal, a signal derived from the patient's ECG signal, the patient's blood pressure, the patient's heartbeat, on-line processing of an image stream of the organ with which the vessel is associated, a location sensor on or within the patient's body, a displacement sensor on or within the patient's body, or any combination thereof.

The aforementioned selected phase of the respiratory cycle may be sensed by a belt placed around the patient's chest, a motion sensor, an oxygenation sensor, a displacement sensor on or within the patient's body, a location sensor on or within the patient's body, or any combination thereof.

In an embodiment, the stepwise advancement of the guide wire is achieved via a guide wire motion modulator (also referred to herein as a "guide wire modulator"). In an embodiment, the guide wire motion modulator is situated outside the patient's body, along the proximal section of the guide wire and proximally to the sheath or guiding catheter through which the guide wire is inserted into the patient's body.

There is therefore provided, in accordance with an embodiment of the present invention, apparatus for use with a portion of a body of a subject that moves as a result of cyclic activity of a body system of the subject, the apparatus including:

a sensor for sensing a phase of the cyclic activity;

a tool configured to be moved with respect to the portion of the subject's body by being pushed by a user; and a tool modulator including:

a gate, configured:

- in a first cycle of the cyclic activity, to allow movement of at least a distal portion of the tool in a distal direction, in response to the sensor sensing that the cyclic activity is at a first given phase thereof,
- following the given phase in the first cycle and prior to an occurrence of the given phase in a subsequent cycle of the cyclic activity, to inhibit the movement of the distal portion of the tool, and
- in a second cycle of the cyclic activity, subsequent to the inhibiting of the movement, to allow movement of the at least the distal portion of the tool in the distal direction, in response to the sensor sensing that the second cycle of the cyclic activity is at the given phase thereof; and an accumulation facilitator configured, following the given phase in the first cycle and prior to the occurrence of the given phase in the subsequent cycle of the cyclic activity, and in response to the user pushing the tool, to facilitate an accumulation selected from the group consisting of: an accumulation of the tool in the tool modulator, and an accumulation of energy in the tool.

In an embodiment, the tool modulator is configured to provide force feedback to the user that is smoothened with respect to the cyclic activity.

In an embodiment, the given phase includes a phase selected from the group consisting of a diastolic phase and an end-diastolic phase, and the gate is configured to allow movement of the distal portion of the tool in the distal direction, in response to the sensor sensing that the cyclic activity is at the selected phase.

In an embodiment, the gate is configured to allow continuous movement of the tool in a proximal direction, when the tool is being withdrawn from the portion of the subject's body.

In an embodiment, the accumulation facilitator includes a pushing element configured to push a portion of the tool at least partially in a non-distal direction, in response to the user pushing the tool in the distal direction.

In an embodiment, the accumulation facilitator is configured to facilitate accumulation of the tool in the tool modulator.

In an embodiment, the accumulation facilitator is configured to facilitate accumulation of energy in the tool.

In an embodiment, the accumulation facilitator is configured to facilitate accumulation of elastic energy in the tool.

In an embodiment, the tool includes a guide wire configured to be moved within a blood vessel of the subject.

In an embodiment:

by allowing movement of at least the distal portion of the tool in the distal direction, the gate is configured to allow movement of a distal portion of the guide wire into a side branch that branches from the blood vessel, when the side branch is at a first angle from the blood vessel, and by inhibiting movement of at least the distal portion of the tool, the gate is configured to inhibit movement of the distal portion of the guide wire into the side branch, when the side branch is at another angle from the blood vessel.

In an embodiment, the gate, by inhibiting the movement of the distal portion of the tool, is configured to inhibit a distal portion of the guide wire from moving in an undesirable direction with respect to the blood vessel.

In an embodiment, the gate, by inhibiting the movement of the distal portion of the tool, is configured to inhibit a distal portion of the guide wire from puncturing the blood vessel.

There is further provided, in accordance with an embodiment of the present invention, a method for automatically controlling movement of a tool when the tool is used with a portion of a body of a subject that moves as a result of cyclic activity of a body system of the subject, the method including:

sensing a phase of the cyclic activity;

in a first cycle of the cyclic activity, allowing movement of at least a distal portion of the tool in a distal direction with respect to the portion, in response to sensing that the cyclic activity is at a first given phase thereof, following the given phase in the first cycle, and prior to an occurrence of the given phase in a subsequent cycle of the cyclic activity:

inhibiting the movement of the distal portion of the tool, and in response to a user pushing the tool, facilitating an accumulation selected from the group consisting of: an accumulation of the tool in a housing, and an accumulation of energy in the tool; and in a second cycle of the cyclic activity, subsequent to the inhibiting of the movement of the distal portion of the tool, allowing movement of the at least the distal portion of the tool in the distal direction, in response to sensing that the second cycle of the cyclic activity is at the given phase thereof.

There is additionally provided, in accordance with an embodiment of the present invention, apparatus for use with a portion of a body of a subject that moves as a result of cyclic activity of a body system of the subject, the apparatus including:

a sensor for sensing a phase of the cyclic activity;

a guide wire configured to be moved with respect to the portion of the subject's body; and a guide wire modulator configured:

in a first cycle of the cyclic activity, to allow movement of at least a distal portion of the guide wire in a distal direction, in response to the sensor sensing that the cyclic activity is at a first given phase thereof, following the given phase in the first cycle and prior to an occurrence of the given phase in a subsequent cycle of the cyclic activity, to inhibit the movement of the distal portion of the guide wire, and in a second cycle of the cyclic activity, subsequent to the inhibiting of the movement, to allow movement of the at least the distal portion of the guide wire in the distal direction, in response to the sensor sensing that the second cycle of the cyclic activity is at the given phase thereof.

In an embodiment, the guide wire modulator is configured to provide force feedback to a user that is smoothened with respect to the cyclic activity.

In an embodiment, the given phase includes a phase selected from the group consisting of a diastolic phase and an end-diastolic phase, and the guide wire modulator is configured to allow movement of the distal portion of the guide wire in the distal direction, in response to the sensor sensing that the cyclic activity is at the selected phase.

In an embodiment, the guide wire modulator is configured to allow continuous movement of the guide wire in a proximal direction, when the guide wire is being withdrawn from the portion of the subject's body.

In an embodiment:

by allowing movement of at least the distal portion of the guide wire in the distal direction, the guide wire modulator is configured to allow movement of the distal portion of the guide wire into a side branch that branches from the blood vessel, when the side branch is at a first angle from the blood vessel, and by inhibiting movement of at least the distal portion of the guide wire, the guide wire modulator is configured to inhibit movement of the distal portion of the guide wire into the side branch, when the side branch is at another angle from the blood vessel.

In an embodiment, the guide wire is configured to be inserted into a blood vessel, and the guide wire modulator, by inhibiting the movement of the distal portion of the tool, is configured to inhibit the guide wire from moving in an undesirable direction with respect to the blood vessel.

In an embodiment, the guide wire, by inhibiting the movement of the distal portion of the tool, is configured to inhibit the guide wire from puncturing the blood vessel.

There is further provided, in accordance with an embodiment of the present invention, a method for use with a portion of a body of a subject that moves as a result of cyclic activity of a body system of the subject, the method including:

sensing a phase of the cyclic activity;

in a first cycle of the cyclic activity, allowing movement of at least a distal portion of a guide wire in a distal direction with respect to the portion, in response to sensing that the cyclic activity is at a first given phase thereof, following the given phase in the first cycle and prior to an occurrence of the given phase in a subsequent cycle of the cyclic activity, inhibiting the movement of the distal portion of the guide wire; and in a second cycle of the cyclic activity, subsequent to the inhibiting of the movement, allowing movement of the at least the distal portion of the guide wire in the distal direction, in response to the sensor sensing that the second cycle of the cyclic activity is at the given phase thereof.

The present invention will be more fully understood from the following detailed description of embodiments thereof, taken together with the drawings, in which:

DETAILED DESCRIPTION OF EMBODIMENTS

Figure 1A:
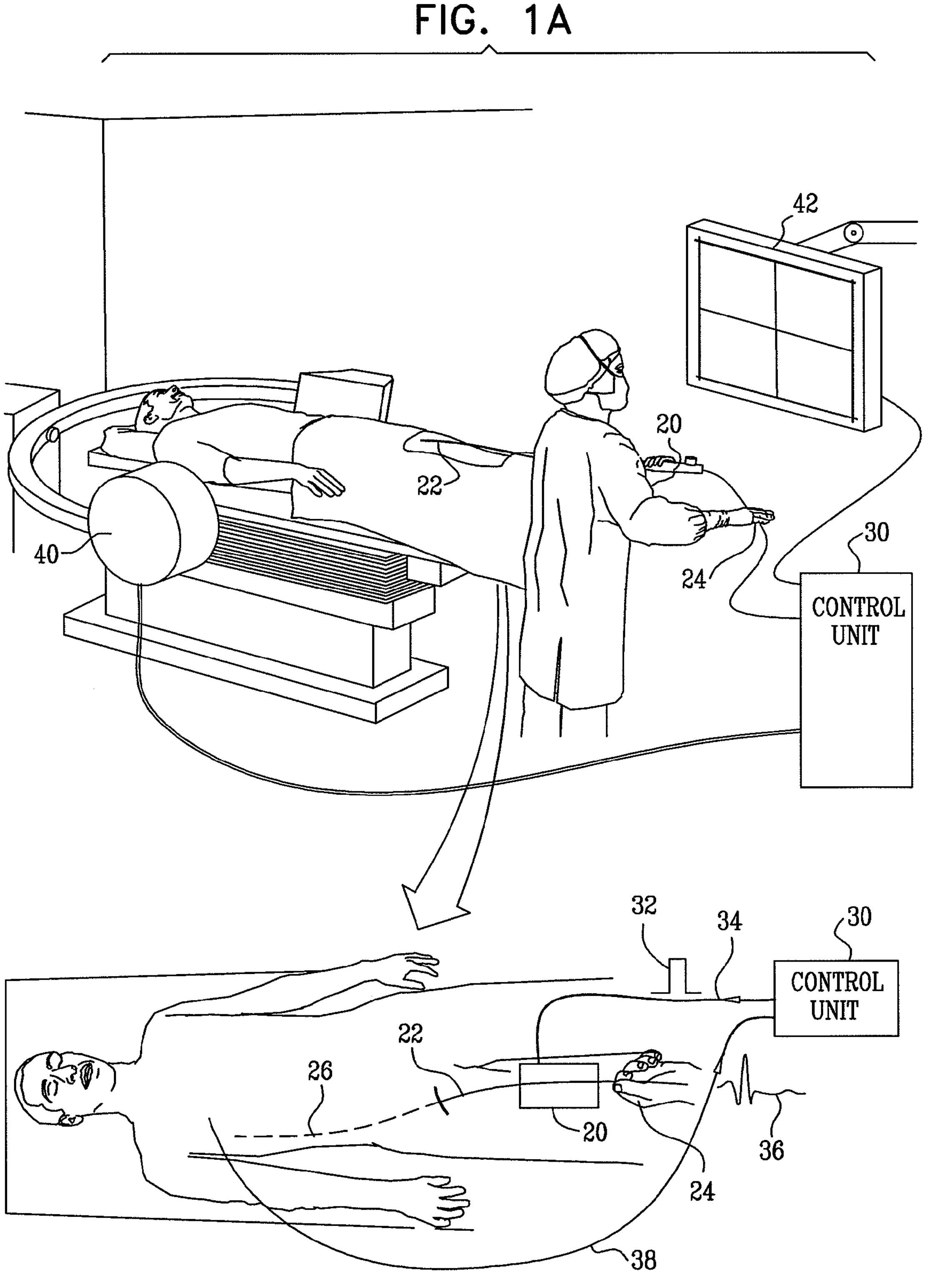
FIGS. 1A and 1B are schematic illustrations of respective views of a guide wire motion modulator being used by a physician, in accordance with an embodiment of the present invention.
Figure 1B:
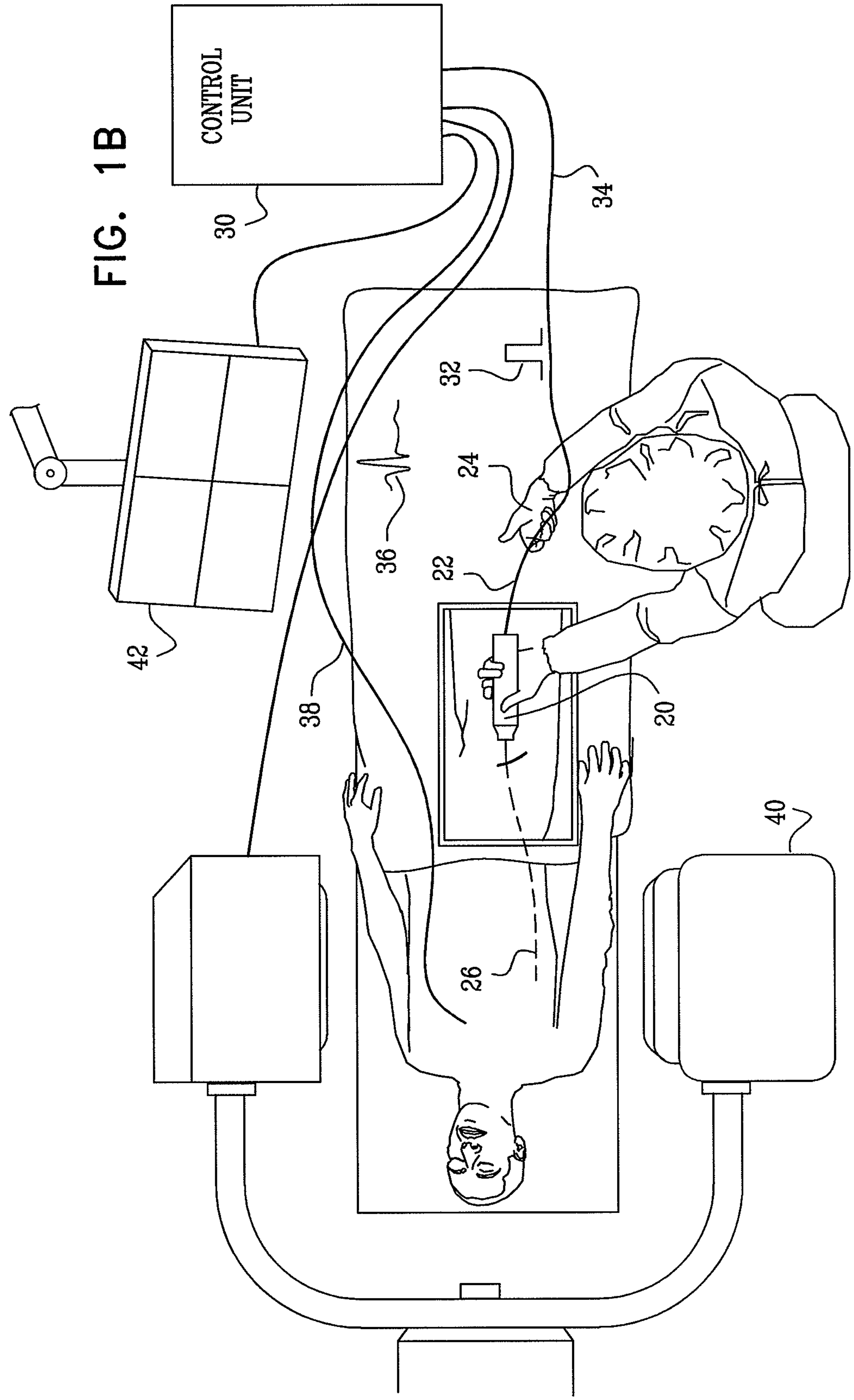

Reference is now made to FIGS. 1A and 1B, which are schematic illustrations of respective views of a guide wire motion modulator 20 being used by a physician, in accordance with an embodiment of the invention. In an embodiment, a tool such as a guide wire 22 is advanced by the physician's hand 24 within arterial system 26 of the patient. The actual forward motion of guide wire 22 is modulated by guide wire motion modulator 20. Guide wire motion modulator 20 receives, from control unit 30, a synchronization signal 32 over a line 34. Control unit 30 derives synchronization signal 32 from an ECG signal 36 of the patient, which is received via a line 38. In an embodiment, the guide wire motion modulator is used for advancing a coronary guide wire. Images of the advancement of guide wire 22 within arterial system 26 of the patient are typically generated by a fluoroscopy system 40 and displayed on a monitor 42. In some embodiments, guide wire 22 is inserted into arterial system 26 via a guiding catheter (not shown), the guiding catheter typically being connected to a proximal side of the apparatus.

Figure 2:
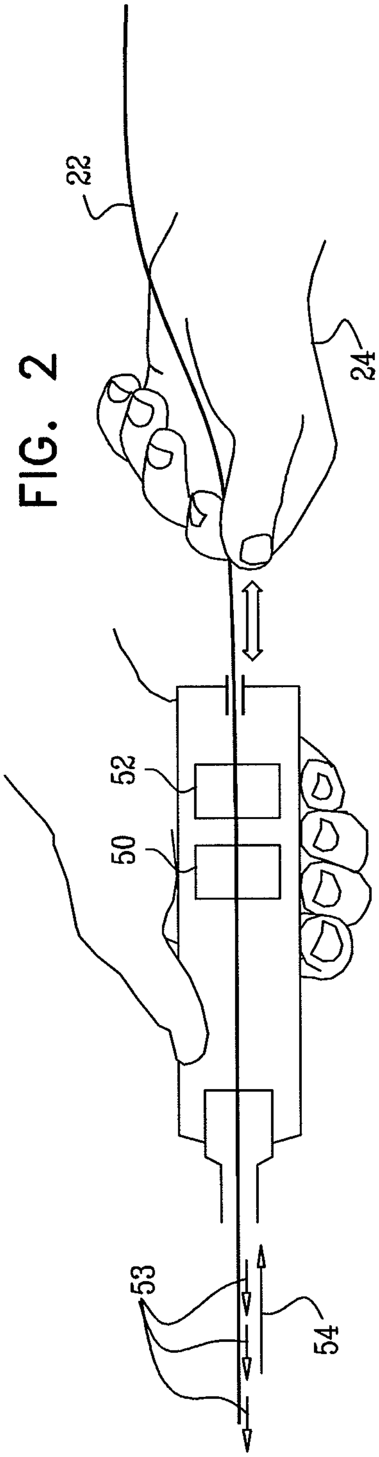
FIGS. 2 and 3 are schematic illustrations of the guide wire motion modulator in operation, in accordance with an embodiment of the present invention.
Figure 3:
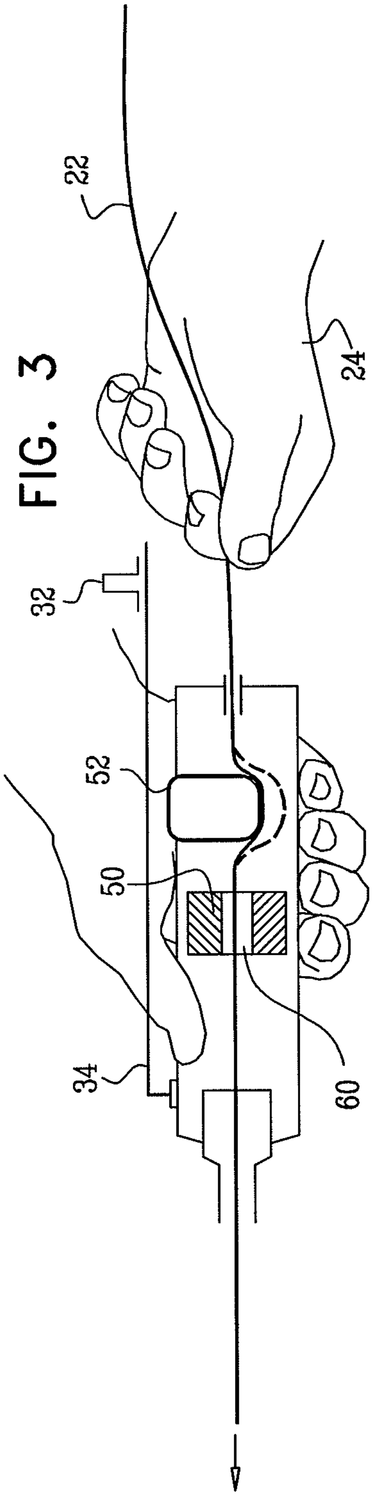

Reference is now made to FIGS. 2 and 3, which are schematic illustrations of guide wire motion modulator 20, in accordance with an embodiment of the present invention. The guide wire motion modulator comprises a housing that contains therein a mechanical gate 50 and an energy and/or material accumulation facilitator 52. Typically, gate 50 is a vise. Guide wire 22 is advanced by physician hand 24 and is inserted through gate 50. Gate 50 is activated (e.g., opened and closed), in synchronization with a measurement of a physiological cycle of the patient, such as the patient's ECG. In an embodiment, the actual forward motion of guide wire 22 is enabled when gate 50 is open and disabled when gate 50 is closed. At times when physician hand 24 pushes guide wire 22 forward while gate 50 is closed, at least some of the energy associated with the pushing of guide wire 22 is accumulated by energy and/or material accumulation facilitator 52 accumulating energy (i.e., elastic energy) in the wire, and, typically, does not result in immediate forward motion of guide wire 22 distally, past the guide wire motion modulator. As shown in FIG. 3, energy and/or material accumulation facilitator 52 typically facilitates the accumulation of a portion of guide wire 22 inside guide wire motion modulator 20. In some embodiments, energy and/or material accumulation facilitator 52 comprises a pushing element such as a knob, as shown. Energy and/or material accumulation facilitator 52 typically facilitates the accumulation of energy and/or material (such as guide wire 22) in response to the guide wire being pushed forwards while gate 50 is closed. The energy and/or material the accumulation of which is facilitated by energy and/or material accumulation facilitator 52, while the gate is closed, is typically released when the gate is subsequently opened. At least a portion of the released energy and/or material is used to advance the guide wire distally. In some embodiments, the guide wire motion modulator is used for advancing a coronary guide wire.

In some embodiments, an outer surface of accumulation facilitator 52 pushes guide wire 22 (as shown), while in other embodiments, guide wire 22 passes through a lumen (not shown) of accumulation facilitator 52, such that movement of the lumen pushes guide wire 22 and thereby facilitates the accumulation of energy and/or material.

Guide wire 22 can typically be pulled back freely when gate 50 is open, for example, when the guide wire is withdrawn from the vessel. For some applications, gate 50 is maintained open continuously during the withdrawal of guide wire 22. For example, guide wire motion modulator 20 may include a sensor (not shown), such as a microswitch, i.e., an electric switch that is able to be actuated by very little physical force. The sensor detects when guide wire 22 is being moved in the proximal direction, and gate 50 is maintained open continuously in response to the sensor detecting that guide wire 22 is being moved in the proximal direction. The stepwise advancement of the guide wire during distal advancement of the guide wire is indicated by arrows 53 of FIG. 2. The continuous movement of the guide wire during withdrawal of the guide wire is indicated by arrow 54 of FIG. 2.

As shown in FIG. 3, guide wire 22 is advanced by physician hand 24 via guide wire motion modulator 20. Specifically, guide wire 22 is inserted via slot 60 in gate 50. The opening and closing of gate 50 is controlled via synchronization signal 32 which is transmitted to guide wire motion modulator 20 via line 34. During a selected phase in the patient's cardiac cycle, and as indicated by signal 32, gate 50 is opened so that when the physician hand 24 pushes guide wire 22 forward, the distal section of guide wire 22 is advanced within the patient's blood vessel. In some embodiments, gate 50 is opened after a defined period of time has elapsed since an event, for example, since when the gate was last closed. In some embodiments, gate 50 is opened after a period of time has elapsed since the gate was previously opened that is equal to the typical length of time of the subject's cardiac cycle. When input synchronization signal 32 indicates that the selected phase in the cardiac cycle is over, or alternatively after a defined period of time has elapsed since an event (for example, after the typical length of time of the selected phase has elapsed since gate 50 was opened), gate 50 closes. Any further pushing of guide wire 22 by physician hand 24 does not result in a forward motion of the distal section of guide wire 22 within the patient's blood vessels. Instead, while gate 50 is closed and guide wire 22 continues to be pushed forward by physician hand 24, knob 52 pushes guide wire 22 sideways (or in a different direction) within the guide wire motion modulator so that the pushing of guide wire 22 by physician hand 24 is translated into curvature of guide wire 22 within the guide wire motion modulator. In some embodiments, at least some of the energy imparted to the guide wire by the physician advancing the guide wire is stored by the guide wire in the form of elastic energy associated with the curvature of guide wire 22. In an embodiment, movement of knob 52 is activated by synchronization signal 32. In an embodiment, knob 52 and gate 50, or parts thereof, are connected rigidly to one another so that they move in tandem. In an embodiment, knob 52 and gate 50 form a single integrated component.

In an embodiment, elements of guide wire motion modulator 20 are powered by an internal power supply, such as a battery. In an embodiment, elements of the guide wire motion modulator are powered by an external power supply. In an embodiment, lines 34 and 38 are wired (as shown in FIG. 1B). In an embodiment, line 34 and/or line 38 is wireless.

Figure 4B:
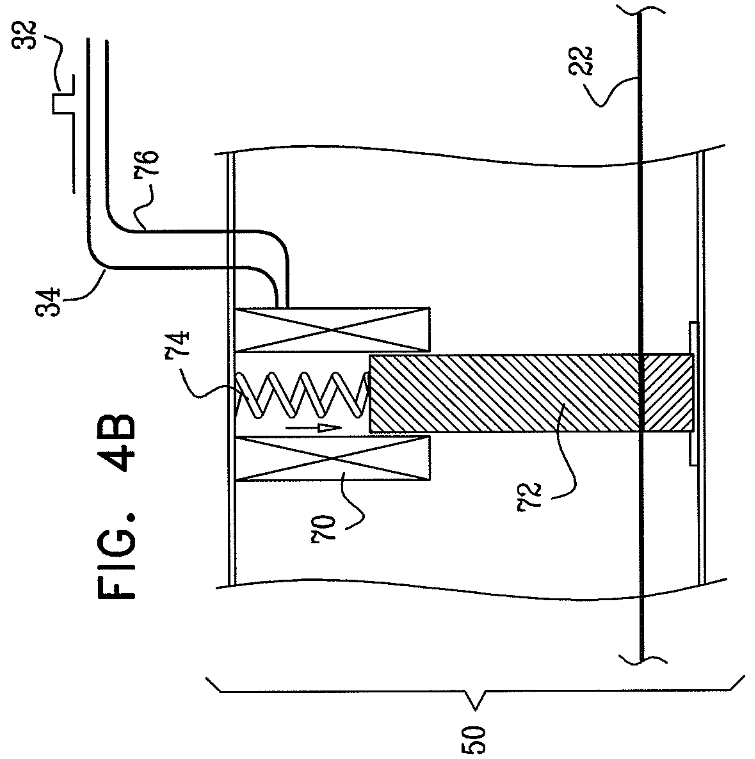
FIGS. 4A and 4B are schematic illustrations of a gate of the guide wire motion modulator, in open and closed configurations, respectively, in accordance with an embodiment of the present invention.
Figure 4A:
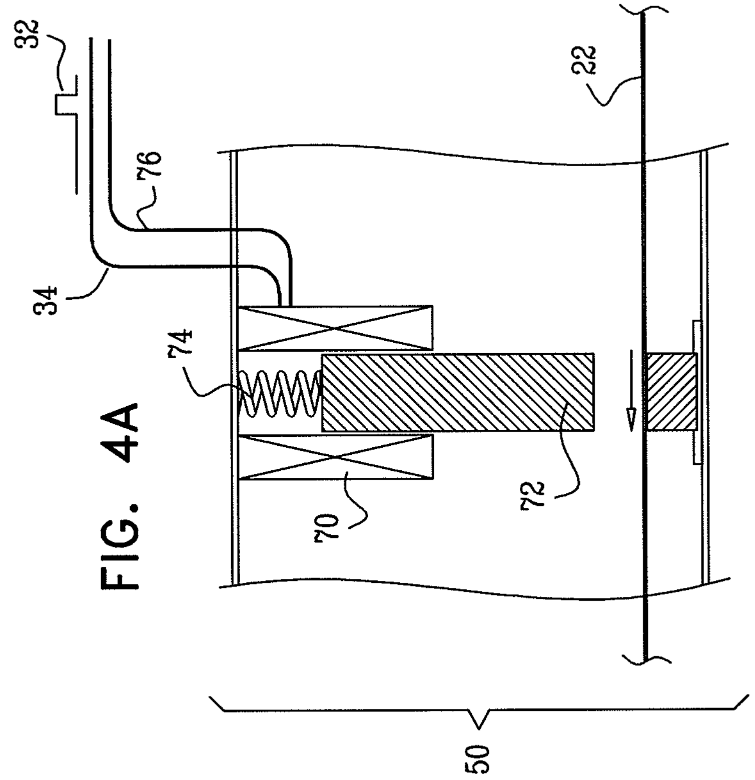

Reference is now made to FIGS. 4A and 4B, which are schematic illustrations of gate 50 of guide wire motion modulator 20, in open and closed configurations, respectively, in accordance with an embodiment of the present invention. In some embodiments, gate 50 is an electromagnetic gate that includes a solenoid 70. As described hereinabove, gate 50 modulates the advancement of guide wire 22. Plunger 72 enables the forward motion of guide wire 22 when in an open position as in FIG. 4A, and, typically, eliminates the forward motion of guide wire 22 when pressed into a closed position, by spring 74, as shown in FIG. 4B.

As shown in FIG. 4A, when signal 32, received via line 34, indicates that the patient's physiological cycle is at (or approximately at) the selected phase in the patient's physiological cycle, solenoid 70, which is powered by line 76, pulls plunger 72 away from guide wire 22 and enables the advancement of guide wire 22.

As shown in FIG. 4B, when signal 32 indicates that the patient's physiological cycle is no longer at the selected phase solenoid 70 releases plunger 72. Plunger 72, having been released by the solenoid, is then pushed by spring 74, such that the plunger squeezes guide wire 22 and hinders advancement of the guide wire.

In some embodiments, solenoid 70 pulls and/or releases plunger 72 after a defined period of time has elapsed since an event. For example, the solenoid may pull and/or release the plunger when a defined period of time has elapsed since the time the gate was previously opened, or closed.

Figure 5A:
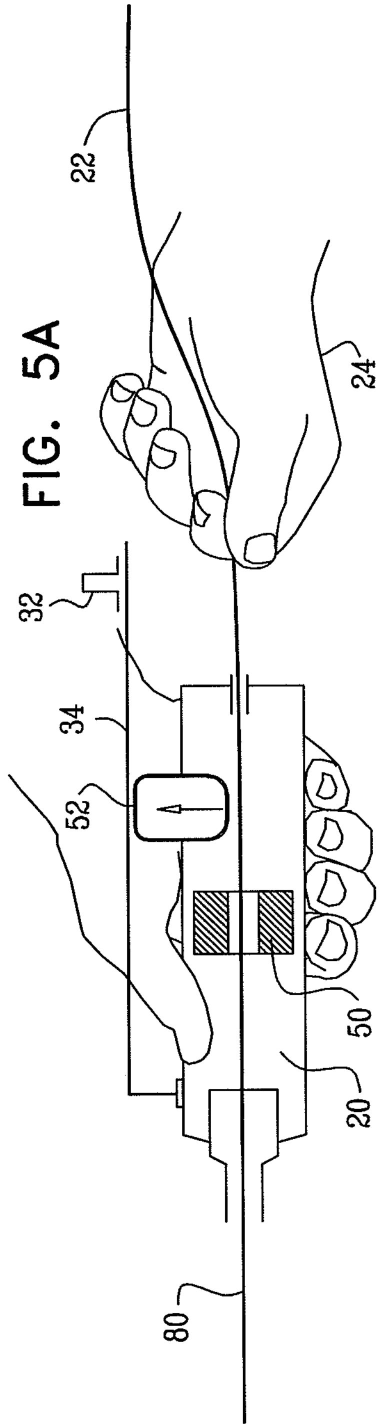
FIGS. 5A-D are schematic illustrations of a sequence of steps in the operation of the guide wire motion modulator, in accordance with an embodiment of the present invention.

Reference is now made to FIGS. 5A-D, which are schematic illustrations of a sequence of steps in the operation of guide wire motion modulator 20, in accordance with an embodiment of the present invention. In FIG. 5A, input synchronization signal 32, received via line 34, indicates that the heart is the selected phase of the cardiac cycle. In an embodiment, the selected phase of the cardiac cycle is a diastolic or end-diastolic phase, when the blood vessels are relatively further spread apart and less twisted. As shown in FIG. 5A, gate 50 is open. In an embodiment, gate 50 includes one or more voice coils that are actuated by synchronization signal 32. In the configuration shown in FIG. 5A, when physician hand 24 pushes guide wire 22 forward, distal section 80 of guide wire 22 is advanced within a portion of the vessel that is distal to the guide wire motion modulator. Knob 52 is positioned near guide wire 22 and, typically, applies substantially no force to guide wire 22.

Figure 5B:
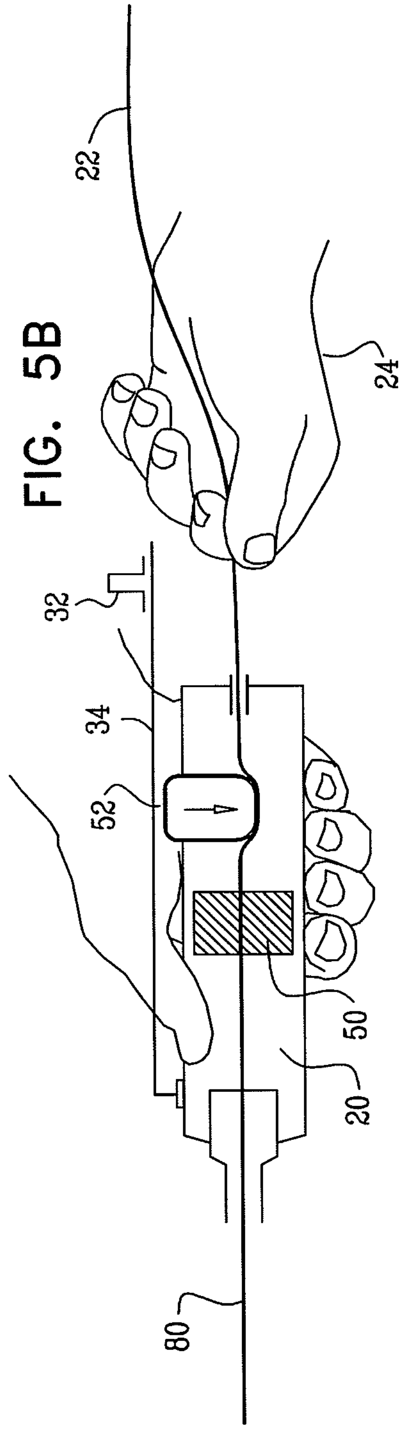

In FIG. 5B, input synchronization signal 32, received via line 34, indicates that the selected phase in the cardiac cycle has ended, has approximately ended, or is about to end. Gate 50 closes, and knob 52 begins to apply a deforming force to guide wire 22. Since the gate is closed, any further pushing of guide wire 22 by physician hand 24 typically does not result in a forward motion of distal section 80 of guide wire 22.

Figure 5C:
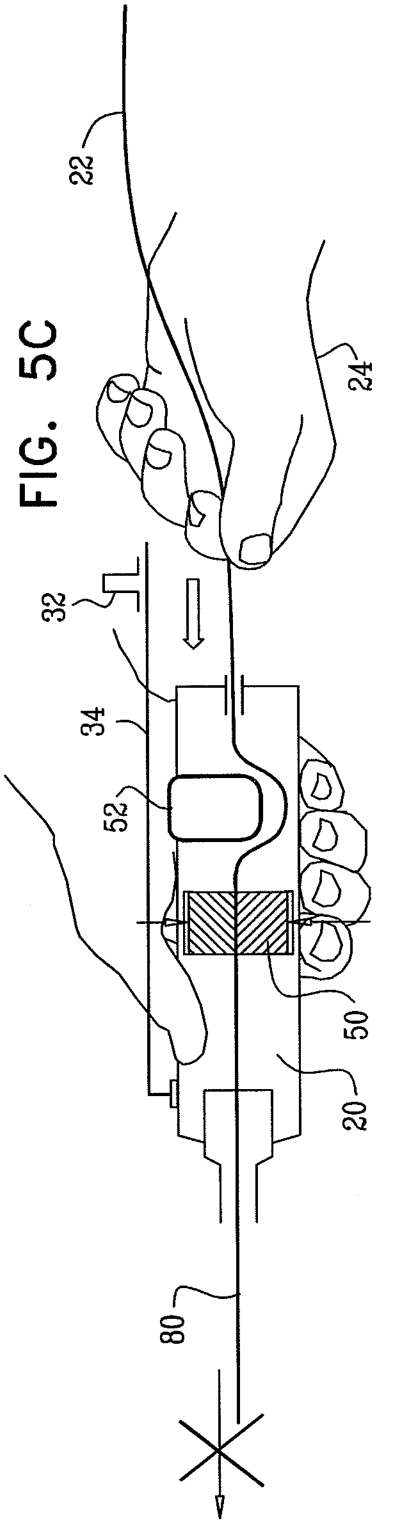

In FIG. 5C, input synchronization signal 32, received via line 34, indicates that the cardiac cycle is still not at the selected phase. As a result, gate 50 is closed, and knob 52 pushes guide wire 22 sideways (or in a different direction that includes a non-forward (i.e., a non-distal) component, such as an upward or a downward component). Any further pushing of guide wire 22 by physician hand 24 typically does not result in a forward motion of distal section 80 of guide wire 22 within the vessel. Instead, any such further pushing of guide wire 22 by physician hand 24 is typically translated into further curvature of guide wire 22. Typically, the curving of the guide wire constitutes an accumulation of elastic energy within the guide wire.

Figure 5D:
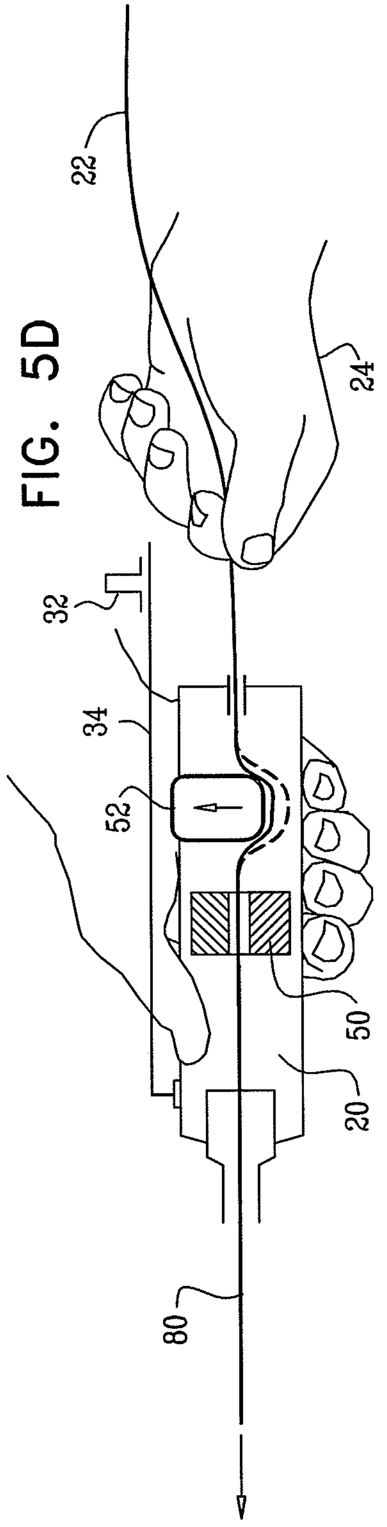

In FIG. 5D, input synchronization signal 32, received via line 34, indicates that the heart is again at, or approximately at, the selected phase of the cardiac cycle. As a result, gate 50 is opened, and knob 52 is released toward its original position, as in FIG. 5A. Typically, the portion of the guide wire that became curved, straightens, thereby releasing the accumulated elastic energy in the form of forward motion of distal section 80 of the guide wire. In an embodiment, the guide wire motion modulator comprises an additional component. When gate 50 is opened, and knob 52 is released, the additional component causes the straightening of guide wire 22 to generate movement of the guide wire in the distal direction (i.e., away from the physician's hand and forward into the patient's body) and not in the proximal direction.

Typically, sequence 5A through 5D is repeated during each cardiac cycle for as long as physician hand 24 pushes guide wire 22 forward. As a result, advancement of distal section 80 of guide wire 22 within the vessel occurs, predominantly, during the selected phase in the cardiac cycle. In some embodiments, gate 50 is configured not to open during the selected phase of every cardiac cycle of the subject. Rather, the gate is configured to open during the selected phase of every Nth cycle, e.g., every second, or third cycle. Alternatively, the gate opens in response to (a) the cardiac cycle being at the selected phase, and (b) another physiological event (e.g., the subject's respiratory cycle being at a selected phase, the subject's heart rate being within a designated range, and/or the subject's blood pressure being within a designated range).

In some embodiments, guide wire motion modulator 20 generates force feedback that does not vary with respect to the cyclic activity of the blood vessel, or force feedback that is smoothened with respect to the cyclic activity of the blood vessel. In an embodiment, physician hand 24 pushes guide wire 22 forward continuously, and, while doing so, the guide wire motion modulator provides feedback to the physician, such that the physician receives continuous sensation of guide wire 22 advancing distally. Conversely, guide wire 22 is actually advanced intermittently, in a stepwise manner and in synchronization with the patient's cardiac cycle.

Figures 6A, 6B, 6C:
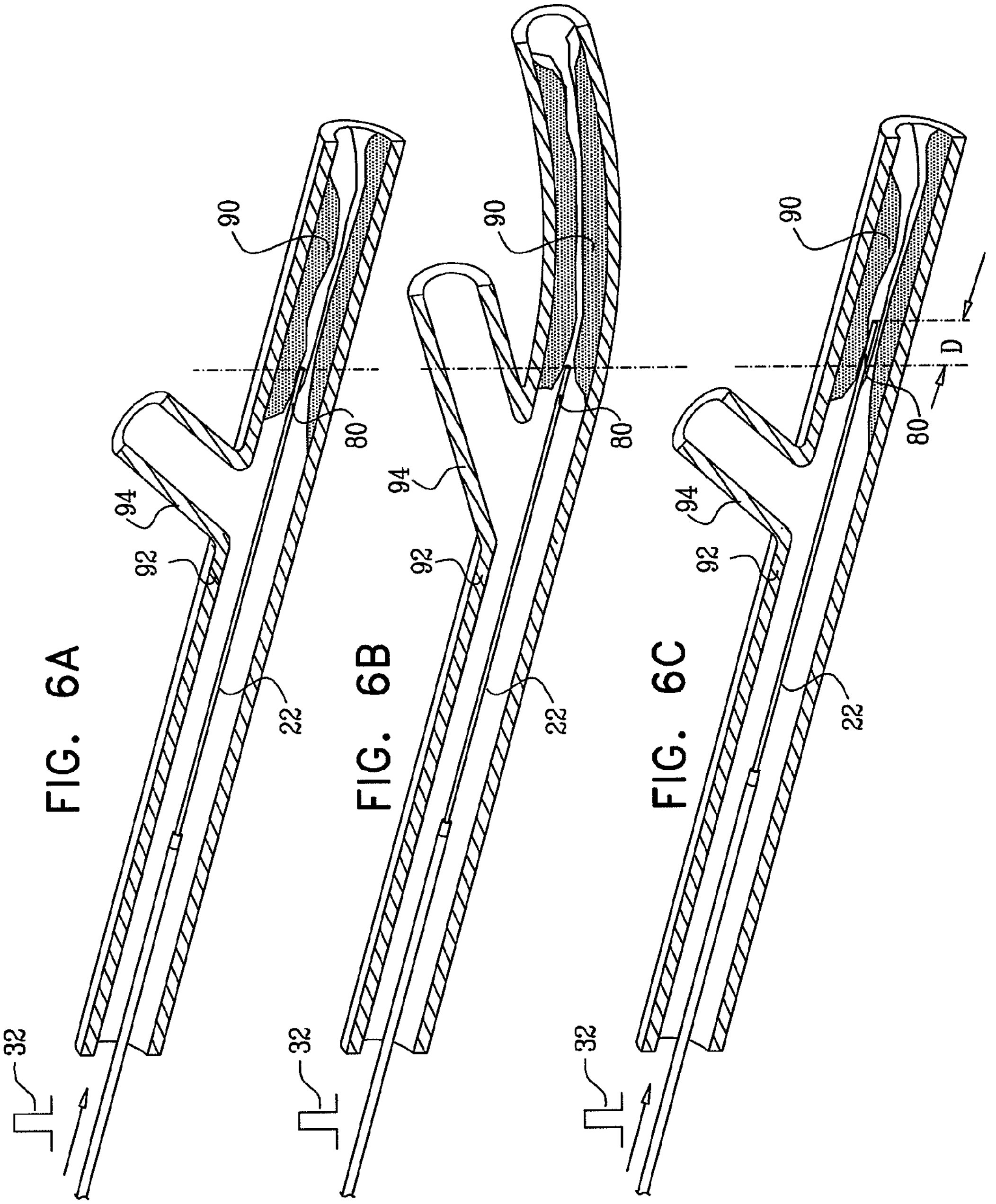
FIGS. 6A-C are schematic illustrations of the forward motion of a guide wire through an occlusion in a vessel, the progress of the guide wire being modulated by a guide wire motion modulator, in accordance with an embodiment of the present invention.

Reference is now made to FIGS. 6A-C, which are schematic illustrations of the forward motion of guide wire 22 through an occlusion 90 in a vessel 92, the progress of the guide wire being modulated by guide wire motion modulator 20, in accordance with an embodiment of the present invention. In an embodiment, the vessel is a coronary artery.

In FIG. 6A, input synchronization signal 32 indicates that the heart is at, or approximately at, the selected phase of the cardiac cycle. In an embodiment, the selected phase of the cardiac cycle is a diastolic or end-diastolic phase, when the coronary arteries are relatively further spread apart and less twisted. The guide wire motion modulator allows distal section 80 of guide wire 22 to advance through occlusion 90 in vessel 92.

In FIG. 6B, input synchronization signal 32 indicates that the cardiac cycle is outside the selected phase. In an embodiment, the guide wire motion modulator is configured to interpret the systolic phase of the cardiac cycle as being outside of the selected phase. In an embodiment, vessel 92 becomes twisted during the systolic phase. During this phase, even when the guide wire is pushed forward by the physician, the guide wire motion modulator does not allow distal section 80 of the guide wire to advance through occlusion 90 in vessel 92.

In FIG. 6C, input synchronization signal 32 indicates that the heart is again at, or approximately at, the selected phase of the cardiac cycle. In an embodiment, the selected phase of the cardiac cycle is a diastolic or end-diastolic phase, when the coronary arteries are relatively further spread apart and less twisted. The guide wire motion modulator allows distal section 80 of the guide wire to advance through occlusion 90 in vessel 92, by a distance D relative to its prior position.

In FIGS. 6A-C, it may be observed that the angle between main blood vessel 92 and side branch 94, which branches from the main blood vessel, is greater during diastole (as shown in FIGS. 6A and 6C) than during systole (as shown in FIG. 6B). As described hereinabove, in some embodiments, guide wire motion modulator 20 is used to facilitate the insertion of guide wire 22 into a side branch, such as side branch 94. For some applications, the guide wire motion modulator allows the guide wire to advance only during a given phase of the cardiac cycle. Typically, this ensures that the angle between the side branch and the main vessel does not vary substantially while the guide wire is advanced into the side branch, thereby facilitating the insertion of the guide wire into the side branch.

U.S. patent application Ser. No. 12/075,244, to Tolkowsky (published as US 2008/0221442), filed Mar. 10, 2008, entitled “Imaging for Use with Moving Organs,” is incorporated herein by reference. In some embodiments, the apparatus and methods described herein are used in conjunction with the apparatus and methods described therein.

U.S. patent application Ser. No. 12/075,214, to Iddan (published as US 2008/0221439), filed Mar. 10, 2008, entitled “Tools for Use with Moving Organs,” is incorporated herein by reference. In some embodiments, the apparatus and methods described herein are used in conjunction with the apparatus and methods described therein.

U.S. patent application Ser. No. 12/075,252, to Iddan (published as US 2008/0221440), filed Mar. 10, 2008, entitled “Imaging and Tools for Use with Moving Organs,” is incorporated herein by reference. In some embodiments, the apparatus and methods described herein are used in conjunction with the apparatus and methods described therein.

Although embodiments relating to endovascular guide wire advancement have been described, the scope of the present invention includes applying the apparatus and methods described herein to other medical tools or probes being moved within, or relative to, a body lumen or organ. For example, embodiments of the present invention may be applied to the advancement of an atherectomy device (e.g., a directional or a rotational atherectomy device) through a coronary artery. In a similar manner to that described with respect to guide wire 22, the advancement of the atherectomy device is synchronized with the subject’s cardiac cycle. During the phase of the cardiac cycle in which advancement of the tool through the subject’s blood vessel is impeded, an energy and/or material accumulation facilitator accumulates energy in the atherectomy device and/or accumulates a portion of the atherectomy device inside an atherectomy device motion modulator. Typically, the atherectomy device is advanced during a phase of the cardiac cycle during which the coronary artery is relatively straight and/or compliant (e.g., the diastolic or end-diastolic phase of the cardiac cycle). Further typically, advancing the atherectomy device during such a phase, and inhibiting advancement of the atherectomy device during other phases of the cardiac cycle, facilitates penetration of an occlusion by the atherectomy device.

Although embodiments have been described according to which the movement of a tool is synchronized with a subject’s cardiac cycle, the scope of the present invention includes synchronizing the movement of a medical tool with a different physiological cycle of the subject, e.g., the subject’s respiratory cycle.

In additional embodiments, the medical tool that is advanced in a stepwise manner includes any one of the following tools, or any combination thereof: a cardiovascular catheter, a stent delivery and/or placement and/or retrieval tool, a balloon delivery and/or placement and/or retrieval tool, a valve delivery and/or placement and/or retrieval tool, a graft delivery and/or placement and/or retrieval tool, a tool for the delivery and/or placement and/or retrieval of an implantable device or of parts of such device, an implantable device or parts thereof, a guide wire, a suturing tool, a biopsy tool, an aspiration tool, a navigational tool, a localization tool, a probe comprising one or more location sensors, a tissue characterization probe, a probe for the analysis of fluid, a measurement probe, an electrophysiological probe, a stimulation probe, an ablation tool, a tool for penetrating or opening partial or total occlusions in blood vessels, a drug or substance delivery tool, a chemotherapy tool, a photodynamic therapy tool, a brachytherapy tool, a local irradiation tool, a laser device, a tool for delivering energy, a tool for delivering markers or biomarkers, a tool for delivering biological glue, an irrigation device, a suction device, a ventilation device, a device for delivering and/or placing and/or retrieving a lead of an electrophysiological device, a lead of an electrophysiological device, a pacing device, an imaging device, a sensing probe, a probe comprising an optical fiber, a robotic tool, a tool that is controlled remotely. In a particular embodiment, techniques described herein are applied to both a guide wire and another tool in this list.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a portion of a body of a subject that moves as a result of cyclic activity of a body system of the subject, the apparatus comprising:

a sensor for sensing a phase of the cyclic activity;

a tool configured to be moved with respect to the portion of the subject’s body by being pushed by a user; and a tool modulator comprising:

a gate, configured:

in a first cycle of the cyclic activity, to allow movement of at least a distal portion of the tool in a distal direction, in response to the sensor sensing that the cyclic activity is at a first given phase thereof, following the given phase in the first cycle and prior to an occurrence of the given phase in a subsequent cycle of the cyclic activity, to inhibit the movement of the distal portion of the tool, and in a second cycle of the cyclic activity, subsequent to the inhibiting of the movement, to allow movement of the at least the distal portion of the tool in the distal direction, in response to the sensor sensing that the second cycle of the cyclic activity is at the given phase thereof; and an accumulation facilitator configured, while the movement of the distal portion of the tool is inhibited by the gate, and in response to the user pushing the tool, to facilitate an accumulation selected from the group consisting of: an accumulation of the tool in the tool modulator, and an accumulation of elastic energy in the tool.

2. The apparatus according to claim 1, wherein the tool modulator is configured to provide force feedback to the user that is smoothened with respect to the cyclic activity.

3. The apparatus according to claim 1, wherein the cyclic activity includes cyclic activity of a cardiac cycle of the subject, wherein the given phase includes a phase selected from the group consisting of a diastolic phase of the cardiac cycle and an end-diastolic phase of the cardiac cycle, and wherein the gate is configured to allow movement of the distal portion of the tool in the distal direction, in response to the sensor sensing that the cardiac cycle is at the selected phase.

4. The apparatus according to claim 1, wherein the gate is configured to allow continuous movement of the tool in a proximal direction, when the tool is being withdrawn from the portion of the subject's body.

5. The apparatus according to claim 1, wherein the accumulation facilitator comprises a pushing element configured to push a portion of the tool at least partially in a non-distal direction, in response to the user pushing the tool in the distal direction.

6. The apparatus according to claim 1, wherein the accumulation facilitator is configured to facilitate accumulation of the tool in the tool modulator.

7. The apparatus according to claim 1, wherein the accumulation facilitator is configured to facilitate accumulation of elastic energy in the tool.

8. The apparatus according to claim 1, wherein the tool comprises a guide wire configured to be moved within a blood vessel of the subject.

9. The apparatus according to claim 8, wherein:

by allowing movement of at least the distal portion of the tool in the distal direction, the gate is configured to allow movement of a distal portion of the guide wire into a side branch that branches from the blood vessel, when the side branch is at a first angle from the blood vessel, and by inhibiting movement of at least the distal portion of the tool, the gate is configured to inhibit movement of the distal portion of the guide wire into the side branch, when the side branch is at another angle from the blood vessel.

10. The apparatus according to claim 8, wherein the gate, by inhibiting the movement of the distal portion of the tool, is configured to inhibit a distal portion of the guide wire from moving in an undesirable direction with respect to the blood vessel.

11. The apparatus according to claim 10, wherein the gate, by inhibiting the movement of the distal portion of the tool, is configured to inhibit a distal portion of the guide wire from puncturing the blood vessel.

12. A method for automatically controlling movement of a tool when the tool is used with a portion of a body of a subject that moves as a result of cyclic activity of a body system of the subject, the method comprising:

sensing a phase of the cyclic activity;

in a first cycle of the cyclic activity, allowing movement of at least a distal portion of the tool in a distal direction with respect to the portion, in response to sensing that the cyclic activity is at a first given phase thereof, following the given phase in the first cycle, and prior to an occurrence of the given phase in a subsequent cycle of the cyclic activity:

inhibiting the movement of the distal portion of the tool, and while the movement of the distal portion of the tool is inhibited, in response to a user pushing the tool, facilitating an accumulation selected from the group consisting of: an accumulation of the tool in a housing, and an accumulation of elastic energy in the tool; and in a second cycle of the cyclic activity, subsequent to the inhibiting of the movement of the distal portion of the tool, allowing movement of the at least the distal portion of the tool in the distal direction, in response to sensing that the second cycle of the cyclic activity is at the given phase thereof, the method being performed using apparatus including:

a sensor for sensing the phase of the cyclic activity;

the tool, the tool being configured to be moved with respect to the portion of the subject's body by being pushed by a user; and a tool modulator including:

a gate, configured:

in the first cycle of the cyclic activity, to allow movement of at least the distal portion of the tool in the distal direction, in response to the sensor sensing that the cyclic activity is at the first given phase thereof, following the given phase in the first cycle and prior to the occurrence of the given phase in the subsequent cycle of the cyclic activity, to inhibit the movement of the distal portion of the tool, and in the second cycle of the cyclic activity, subsequent to the inhibiting of the movement, to allow movement of the at least the distal portion of the tool in the distal direction, in response to the sensor sensing that the second cycle of the cyclic activity is at the given phase thereof; and an accumulation facilitator configured, while the movement of the distal portion of the tool is inhibited by the gate, and in response to the user pushing the tool, to facilitate the selected accumulation.

13. The method according to claim 12, further comprising providing force feedback to the user that is smoothened with respect to the cyclic activity.

14. The method according to claim 12, wherein the cyclic activity includes cyclic activity of a cardiac cycle of the subject, wherein the given phase includes a phase selected from the group consisting of a diastolic phase of the cardiac cycle and an end-diastolic phase of the cardiac cycle, and wherein allowing movement of the distal portion of the tool in the distal direction comprises allowing movement of the distal portion of the tool in the distal direction, in response to sensing that the cardiac cycle is at the selected phase.

15. The method according to claim 12, further comprising allowing continuous movement of the tool in a proximal direction, when the tool is being withdrawn from the portion of the subject's body.

16. The method according to claim 12, wherein facilitating the accumulation comprises pushing a portion of the tool at least partially in a non-distal direction, in response to the user pushing the tool.

17. The method according to claim 12, wherein facilitating the accumulation comprises facilitating accumulation of the tool in the housing.

18. The method according to claim 12, wherein facilitating the accumulation comprises facilitating accumulation of elastic energy in the tool.

19. The method according to claim 12, wherein the tool includes a guide wire configured to be moved within a blood vessel of the subject, and wherein allowing movement of at least the distal portion of the tool with respect to the portion comprises allowing movement of at least a distal portion of the guide wire within the blood vessel.

20. The method according to claim 19, wherein:

allowing movement of at least the distal portion of the tool in the distal direction comprises allowing movement of a distal portion of the guide wire into a side branch that branches from the blood vessel, when the side branch is at a first angle from the blood vessel, and inhibiting the movement of at least the distal portion of the tool comprises inhibiting movement of the distal portion of the guide wire into the side branch, when the side branch is at another angle from the blood vessel.

21. The method according to claim 19, wherein inhibiting the movement of the distal portion of the tool comprises inhibiting the guide wire from moving in an undesirable direction with respect to the blood vessel.

22. The method according to claim 21, wherein inhibiting the movement of the distal portion of the tool comprises inhibiting the guide wire from puncturing the blood vessel.

23. Apparatus for use with a portion of a body of a subject that moves as a result of cyclic activity of a body system of the subject, the apparatus comprising:

a sensor for sensing a phase of the cyclic activity;

a guide wire configured to be moved with respect to the portion of the subject's body;

a guide wire modulator configured:

in a first cycle of the cyclic activity, to allow movement of at least a distal portion of the guide wire in a distal direction, in response to the sensor sensing that the cyclic activity is at a first given phase thereof, following the given phase in the first cycle and prior to an occurrence of the given phase in a subsequent cycle of the cyclic activity, to inhibit the movement of the distal portion of the guide wire, and in a second cycle of the cyclic activity, subsequent to the inhibiting of the movement, to allow movement of the at least the distal portion of the guide wire in the distal direction, in response to the sensor sensing that the second cycle of the cyclic activity is at the given phase thereof; and an accumulation facilitator configured, while the movement of the distal portion of the guide wire is inhibited by the guide wire modulator, and in response to a user pushing the guide wire, to facilitate an accumulation selected from the group consisting of: an accumulation of the guide wire in the guide wire modulator, and an accumulation of elastic energy in the guide wire.

24. The apparatus according to claim 23, wherein the guide wire modulator is configured to provide force feedback to the user that is smoothened with respect to the cyclic activity.

25. The apparatus according to claim 23, wherein the cyclic activity includes cyclic activity of a cardiac cycle of the subject, wherein the given phase includes a phase selected from the group consisting of a diastolic phase of the cardiac cycle and an end-diastolic phase of the cardiac cycle, and wherein the guide wire modulator is configured to allow movement of the distal portion of the guide wire in the distal direction, in response to the sensor sensing that the cardiac cycle is at the selected phase.

26. The apparatus according to claim 23, wherein the guide wire modulator is configured to allow continuous movement of the guide wire in a proximal direction, when the guide wire is being withdrawn from the portion of the subject's body.

27. The apparatus according to claim 23, wherein:

by allowing movement of at least the distal portion of the guide wire in the distal direction, the guide wire modulator is configured to allow movement of the distal portion of the guide wire into a side branch that branches from the blood vessel, when the side branch is at a first angle from the blood vessel, and by inhibiting movement of at least the distal portion of the guide wire, the guide wire modulator is configured to inhibit movement of the distal portion of the guide wire into the side branch, when the side branch is at another angle from the blood vessel.

28. The apparatus according to claim 23, wherein the guide wire is configured to be inserted into a blood vessel, and wherein the guide wire modulator, by inhibiting the movement of the distal portion of the guide wire, is configured to inhibit the guide wire from moving in an undesirable direction with respect to the blood vessel.

29. The apparatus according to claim 28, wherein the guide wire modulator, by inhibiting the movement of the distal portion of the guide wire, is configured to inhibit the guide wire from puncturing the blood vessel.

30. A method for use with a portion of a body of a subject that moves as a result of cyclic activity of a body system of the subject, the method comprising:

sensing a phase of the cyclic activity;

in a first cycle of the cyclic activity, allowing movement of at least a distal portion of a guide wire in a distal direction with respect to the portion, in response to sensing that the cyclic activity is at a first given phase thereof, following the given phase in the first cycle and prior to an occurrence of the given phase in a subsequent cycle of the cyclic activity, inhibiting the movement of the distal portion of the guide wire, and while the movement of the distal portion of the guide wire is inhibited, in response to a user pushing the guide wire, facilitating an accumulation selected from the group consisting of: an accumulation of the guide wire in a housing, and an accumulation of elastic energy in the guide wire; and in a second cycle of the cyclic activity, subsequent to the inhibiting of the movement, allowing movement of the at least the distal portion of the guide wire in the distal direction, in response to the sensor sensing that the second cycle of the cyclic activity is at the given phase thereof, the method being performed using apparatus, including:

a sensor for sensing the phase of the cyclic activity;

the guide wire, the guide wire being configured to be moved with respect to the portion of the subject's body; and a guide wire modulator configured:

in the first cycle of the cyclic activity, to allow movement of at least the distal portion of the guide wire in the distal direction, in response to the sensor sensing that the cyclic activity is at the first given phase thereof, following the given phase in the first cycle and prior to the occurrence of the given phase in the subsequent cycle of the cyclic activity, to inhibit the movement of the distal portion of the guide wire, and in the second cycle of the cyclic activity, subsequent to the inhibiting of the movement, to allow movement of the at least the distal portion of the guide wire in the distal direction, in response to the sensor sensing that the second cycle of the cyclic activity is at the given phase thereof; and an accumulation facilitator configured, while the movement of the distal portion of the guide wire is inhibited by the guide wire modulator, and in response to the user pushing the guide wire, to facilitate the selected accumulation.

31. The method according to claim 30, further comprising providing force feedback to the user that is smoothened with respect to the movement of the portion of the subject's body.

32. The method according to claim 30, wherein the cyclic activity includes cyclic activity of a cardiac cycle of the subject, wherein the given phase includes a phase selected from the group consisting of a diastolic phase of the cardiac cycle and an end-diastolic phase of the cardiac cycle, and wherein allowing movement of the distal portion of the guide wire in the distal direction, comprises allowing movement of the distal portion of the guide wire in the distal direction, in response to sensing that the cardiac cycle is at the selected phase.

33. The method according to claim 30, further comprising allowing continuous movement of the guide wire in a proximal direction, when the guide wire is being withdrawn from the portion of the subject's body.

34. The method according to claim 30, wherein:

allowing movement of at least the distal portion of the guide wire in the distal direction, comprises allowing movement of the distal portion of the guide wire into a side branch that branches from a main blood vessel, when the side branch is at a first angle from the blood vessel, and inhibiting the movement of at least the distal portion of the guide wire comprises inhibiting movement of the distal portion of the guide wire into the side branch, when the side branch is at another angle from the blood vessel.

35. The method according to claim 30, wherein the guide wire is configured to be moved within a blood vessel of the subject, and wherein inhibiting the movement of the distal portion of the guide wire comprises inhibiting the guide wire from moving in an undesirable direction with respect to the blood vessel.

36. The method according to claim 35, wherein inhibiting the movement of the distal portion of the guide wire comprises inhibiting the guide wire from puncturing the blood vessel.

* * * * *